US012558173B2

(12) United States Patent
Seo et al.

(10) Patent No.: US 12,558,173 B2
(45) Date of Patent: Feb. 24, 2026

(54) VASCULAR INTERVENTION ROBOT AND VASCULAR INTERVENTION SYSTEM HAVING LINE-CONTACT ROLLER MECHANISM

(71) Applicant: PERAZAH INC., Ansan-si (KR)

(72) Inventors: Jong Tae Seo, Gwangju-si (KR); Hwan Taek Ryu, Ansan-si (KR)

(73) Assignee: PERAZAH INC., Ansan-si (KR)

( * ) Notice: Subject to any disclaimer, the term of this patent is extended or adjusted under 35 U.S.C. 154(b) by 327 days.

(21) Appl. No.: 18/272,800

(22) PCT Filed: Jan. 19, 2022

(86) PCT No.: PCT/KR2022/000962
§ 371 (c)(1),
(2) Date: Jul. 18, 2023

(87) PCT Pub. No.: WO2022/158840
PCT Pub. Date: Jul. 28, 2022

(65) Prior Publication Data
US 2024/0081924 A1 Mar. 14, 2024

(30) Foreign Application Priority Data

Jan. 19, 2021 (KR) ........................ 10-2021-0007643

(51) Int. Cl.
*A61B 34/30* (2016.01)
*A61M 25/09* (2006.01)

(52) U.S. Cl.
CPC ........ *A61B 34/30* (2016.02); *A61B 2034/301* (2016.02); *A61B 2034/303* (2016.02); *A61M 25/09041* (2013.01)

(58) Field of Classification Search
CPC .............. A61B 34/30; A61B 2034/301; A61B 2034/303; A61B 17/00234;
(Continued)

(56) References Cited

U.S. PATENT DOCUMENTS 8,187,229 B2 5/2012 Weitzner et al.
2007/0239106 A1 10/2007 Weitzner et al.

FOREIGN PATENT DOCUMENTS

JP 2019512319 A 5/2019
KR 20140005236 U 10/2014
(Continued)

OTHER PUBLICATIONS

International search report of PCT/KR2022/000962, May 4, 2022, English translation of abstract.

*Primary Examiner* — Richard G Louis
(74) *Attorney, Agent, or Firm* — STIP Law Group, LLC

(57) ABSTRACT

A vascular intervention robot having a line-contact roller mechanism is provided. The vascular intervention robot having a line-contact roller mechanism comprises: a roller module for translating a medical wire; and a rotation module for axially rotating the medical wire by rotating the roller module. The roller module can comprise: a translational motor providing a translational driving force for translating the medical wire; at least one drive roller receiving a translational driving force from the translational motor, arrayed in the length direction of the medical wire, and rolling-contacted with the lower part of the medical wire; and a guide roller provided in a number corresponding to the drive roller, arrayed above the drive roller and in the length direction of the medical wire, shifted to one side in the length direction of the medical wire with respect to the drive roller, and rolling-contacted with the upper part of the medical wire. Therefore, the vascular intervention robot having a line-contact roller mechanism can be provided which can minimize slip of the medical wire when the medical wire is axially rotated in accordance with the rotation of the roller module due to the rotation module, and (Continued)

also can minimize slip of the medical wire when translation-moved by means of the roller module.

14 Claims, 22 Drawing Sheets

(58) Field of Classification Search
CPC ........ A61M 25/09041; A61M 25/0113; A61M 2025/0042; A61M 2025/09116
See application file for complete search history.

(56) References Cited

FOREIGN PATENT DOCUMENTS

| | | |
|---|---|---|
| KR | 20160136904 A | 11/2016 |
| KR | 20170000178 A | 1/2017 |
| KR | 20190121928 A | 10/2019 |
| KR | 20200081224 A | 7/2020 |

[FIG. 1]
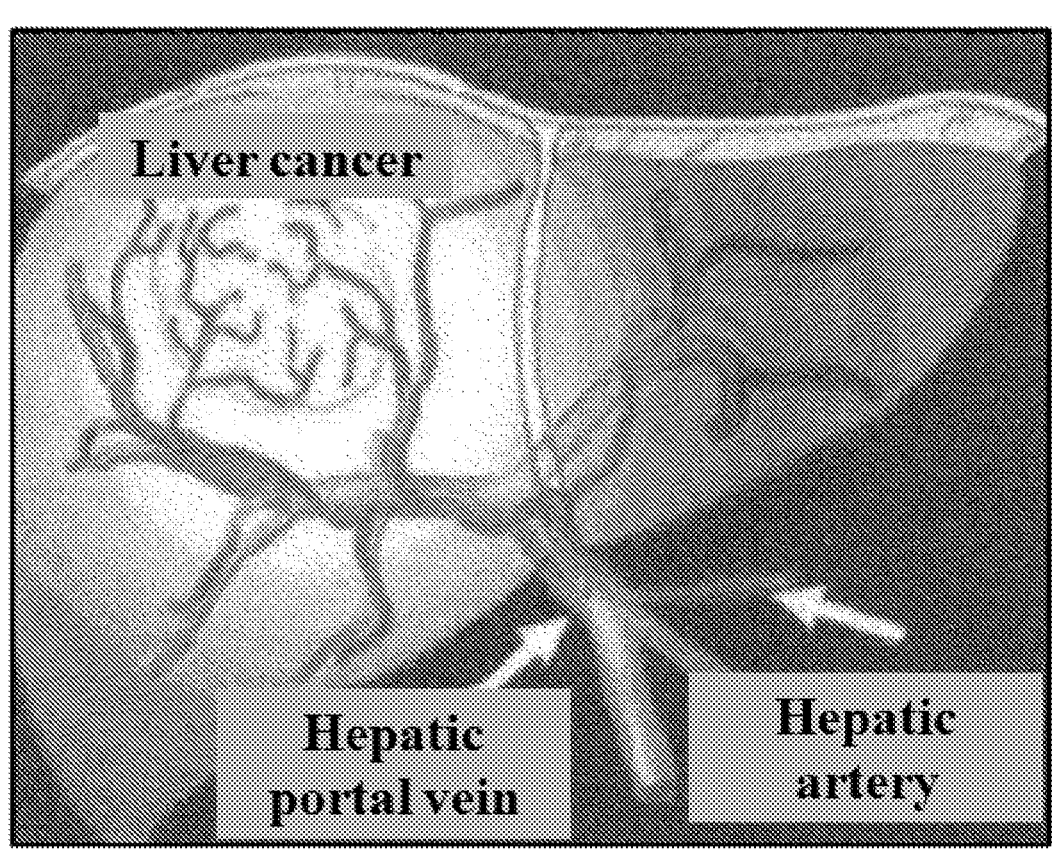

[FIG. 2]
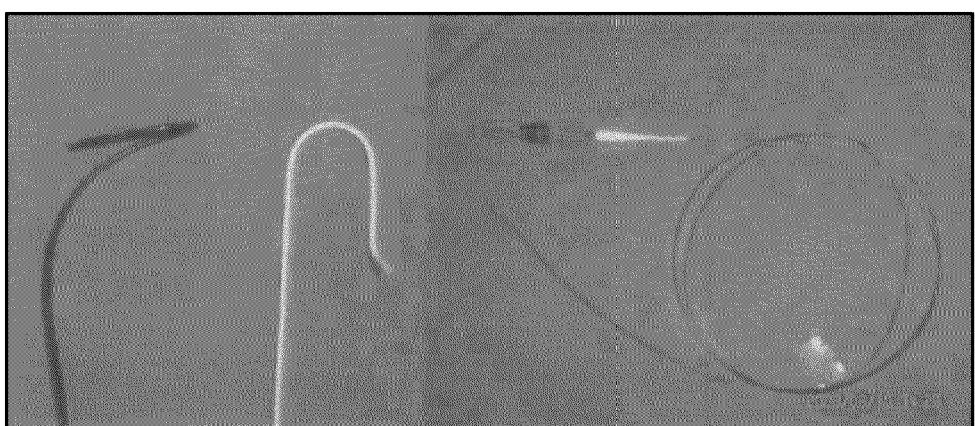

[FIG. 3]
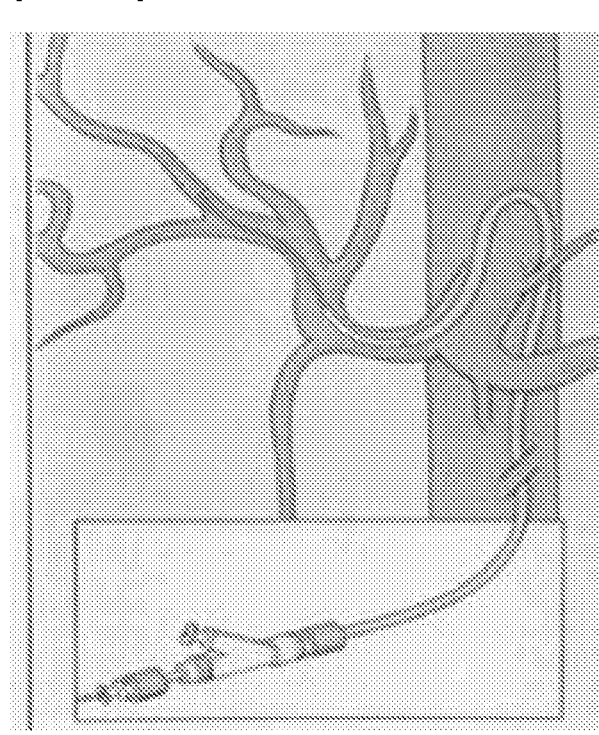

[FIG. 4]

[FIG. 5]
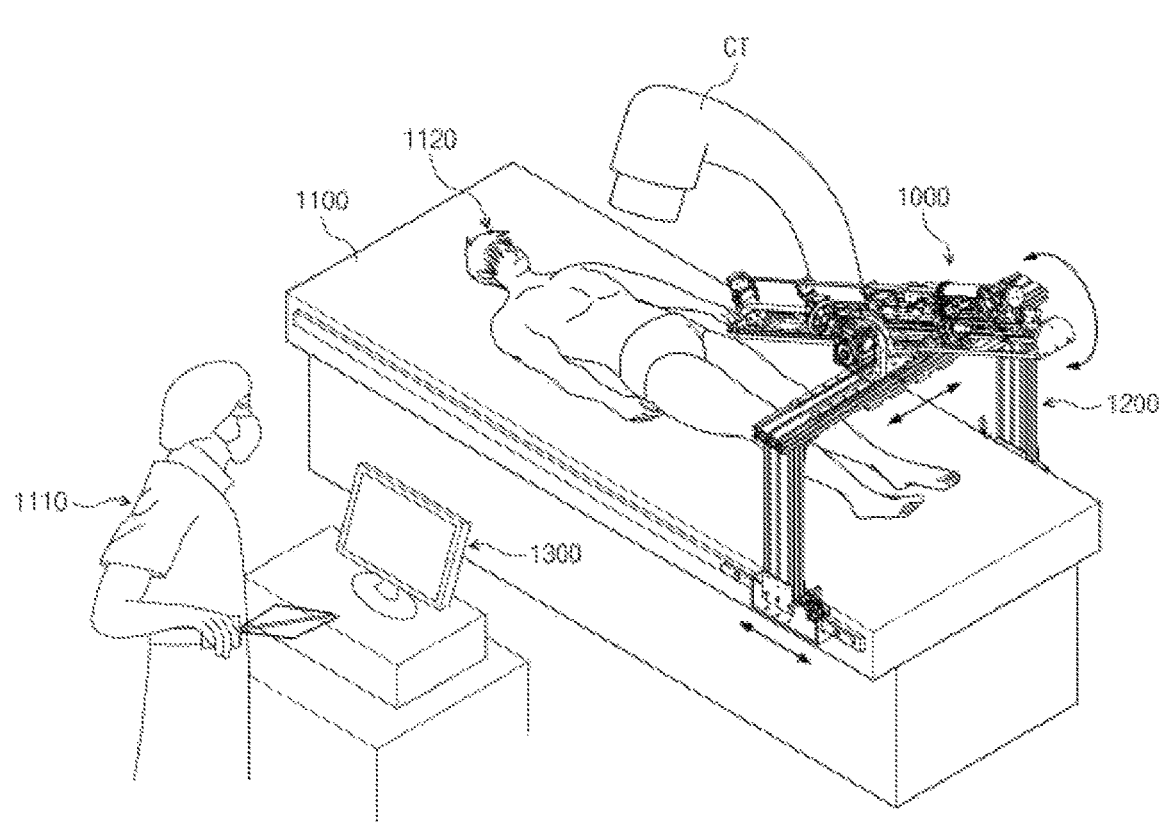

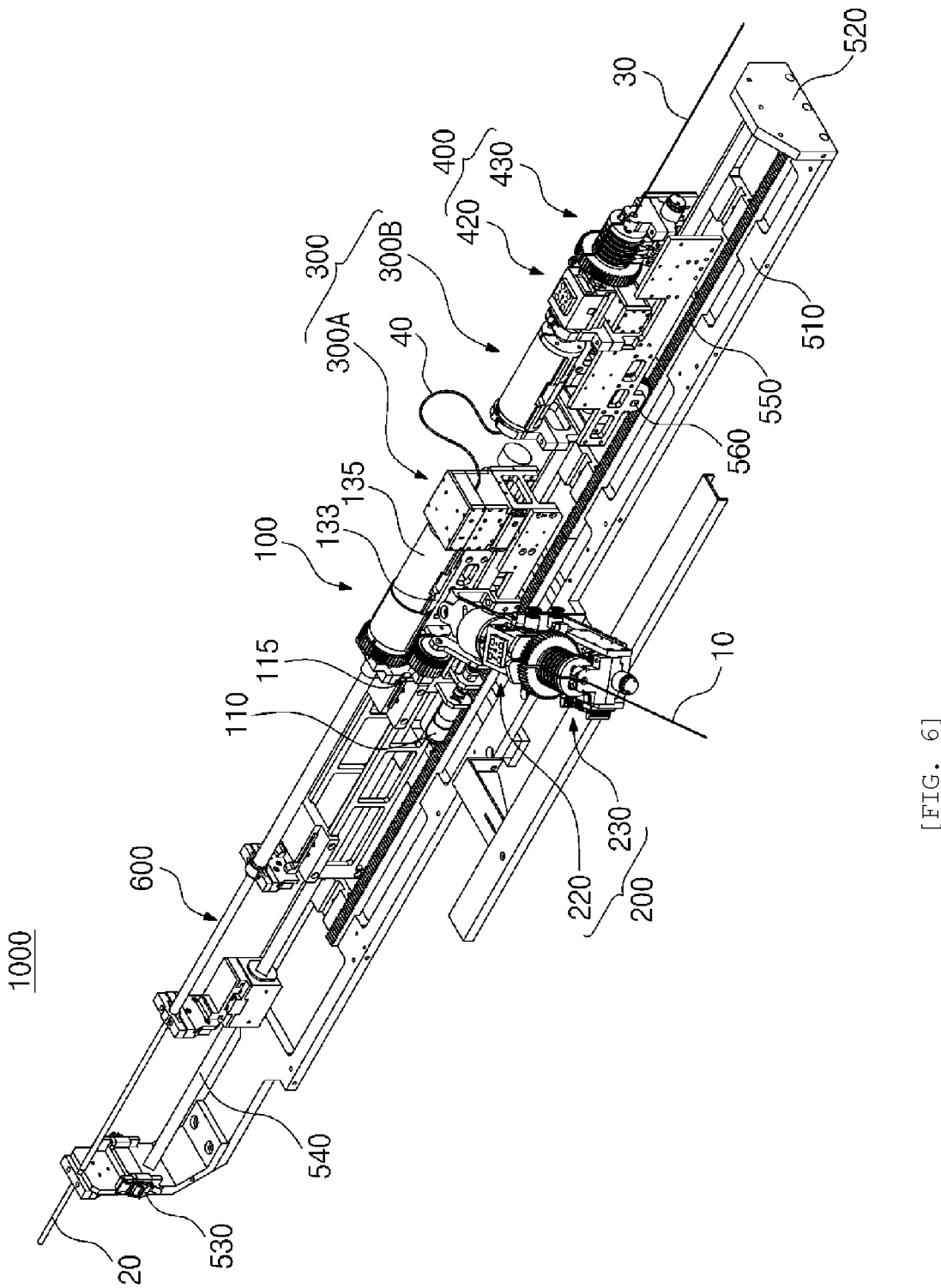
[FIG. 6]

[FIG. 7]
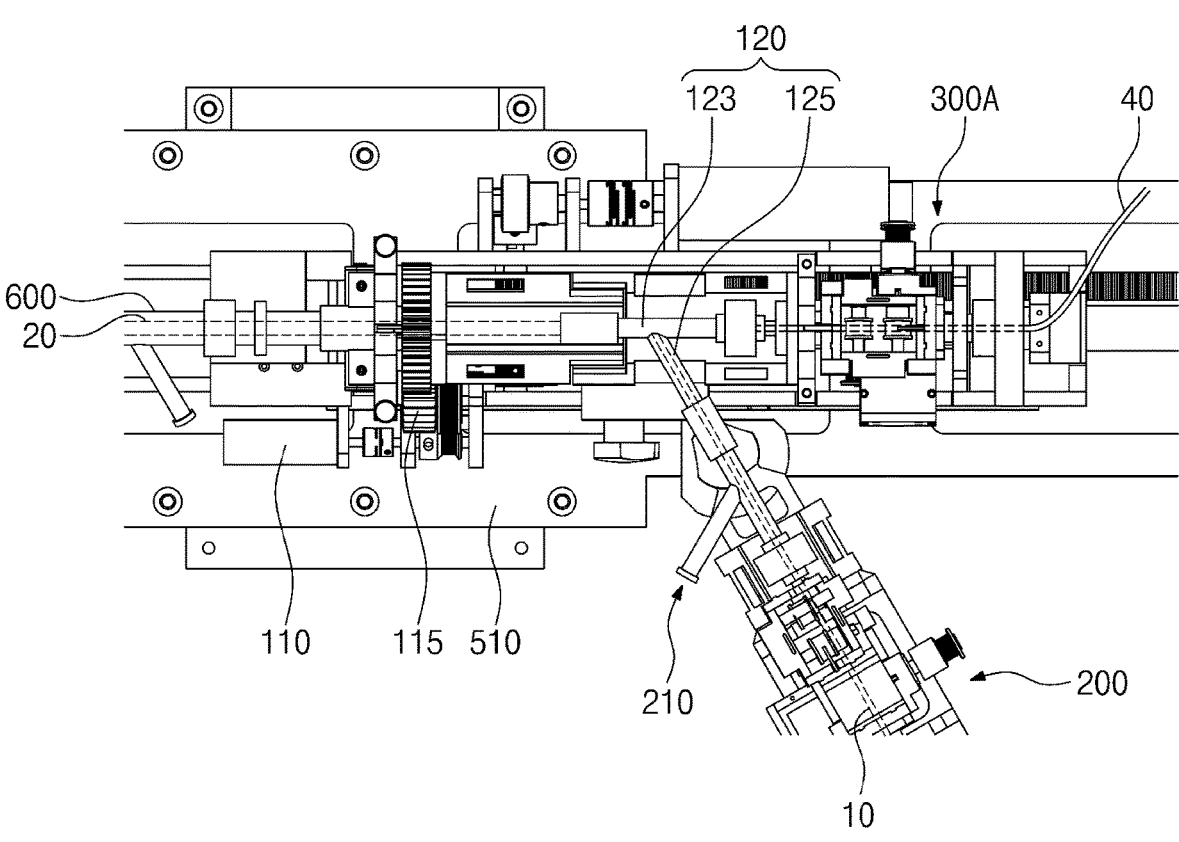

[FIG. 8]
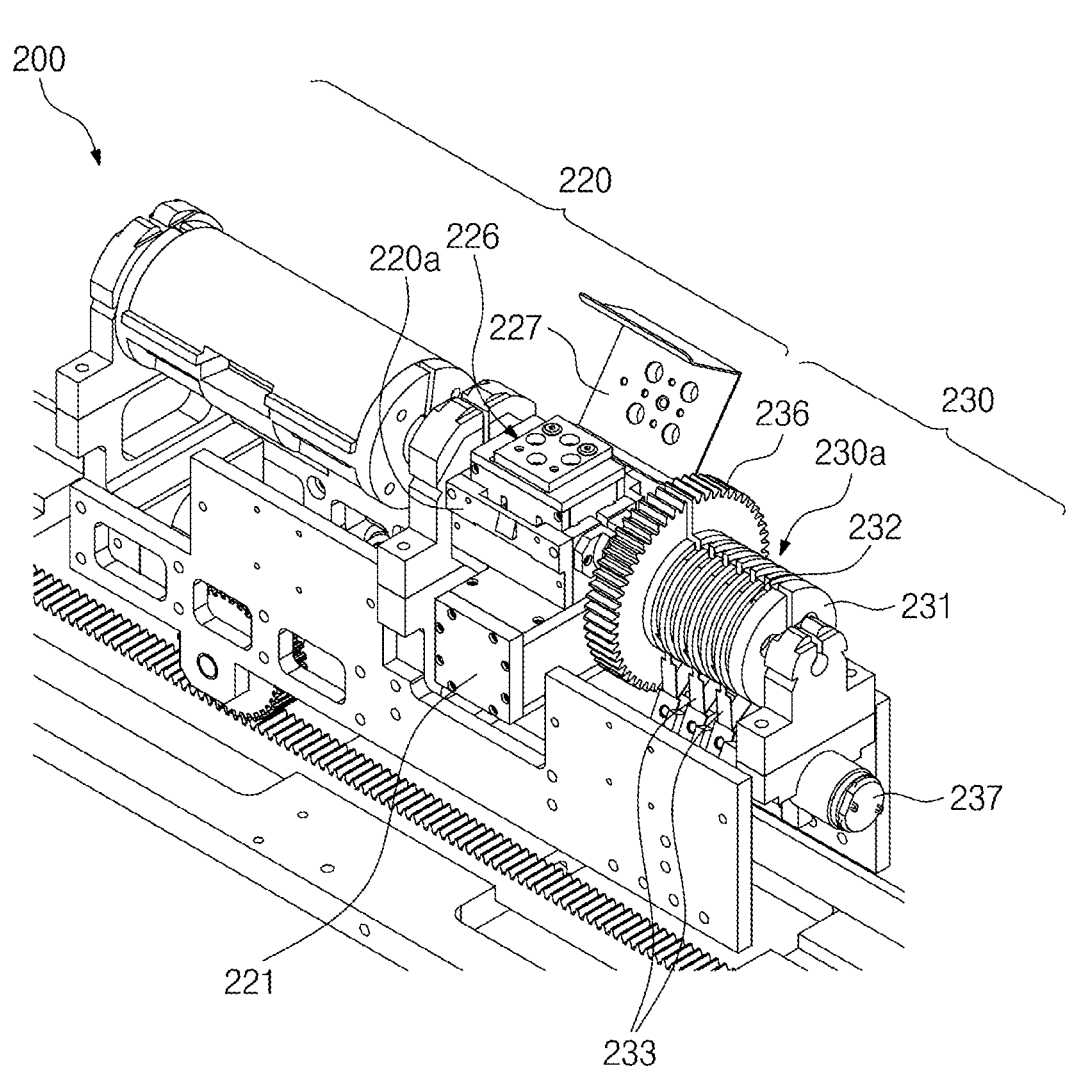

[FIG. 9]
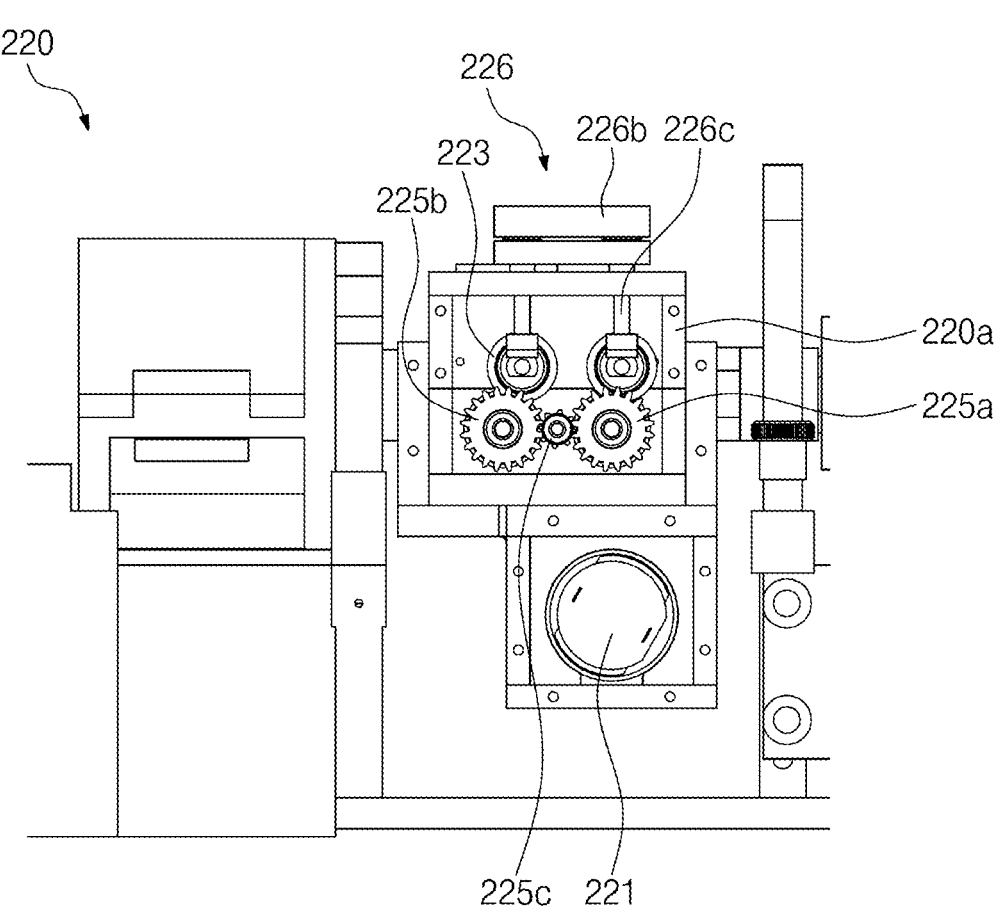

[FIG. 10]
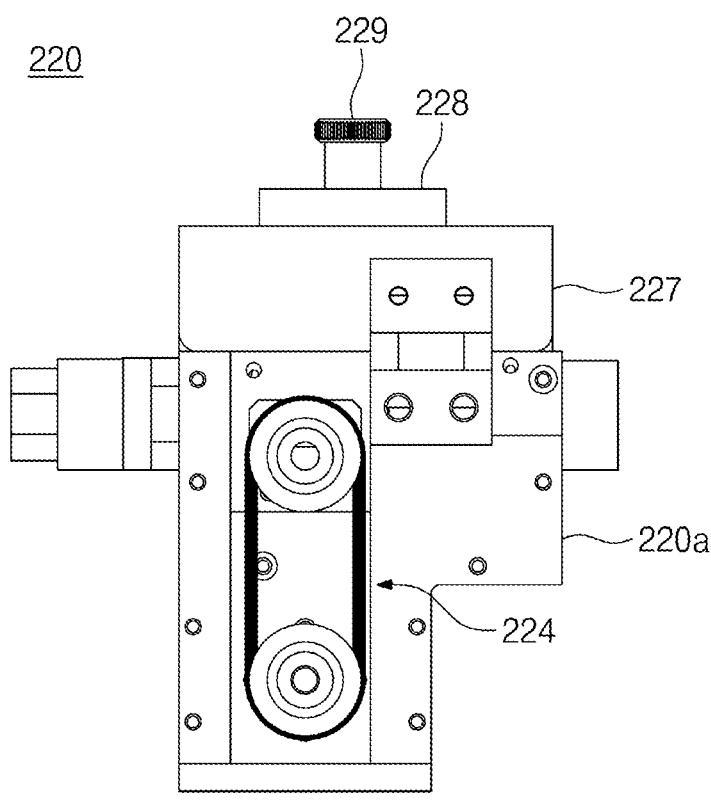

[FIG. 11]
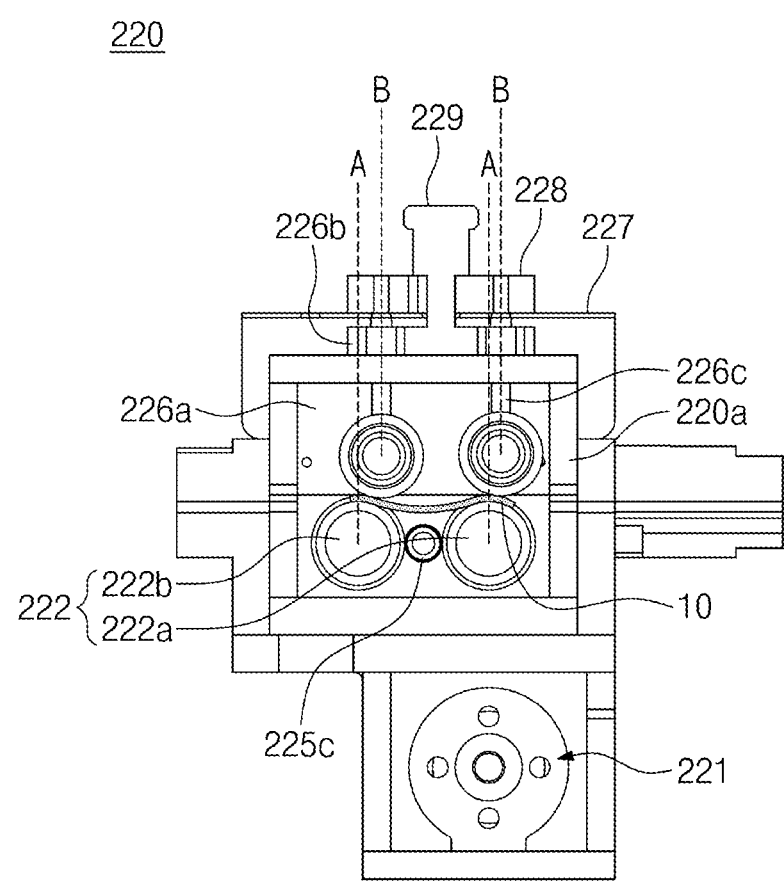

[FIG. 12]
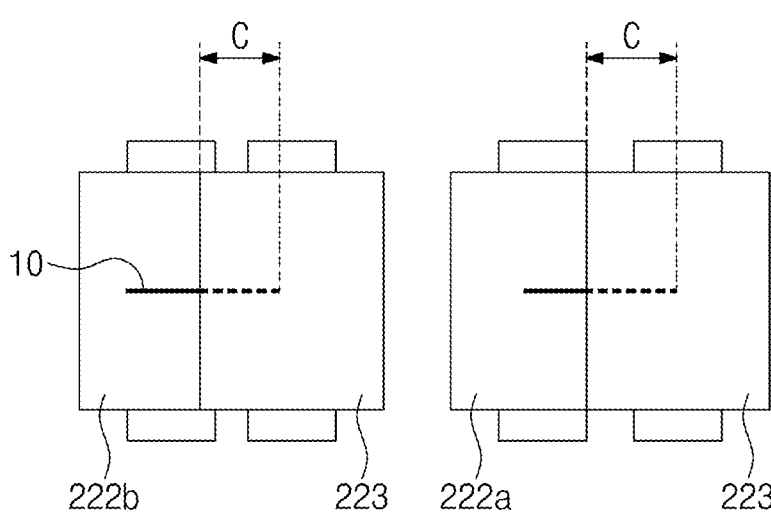

[FIG. 13]
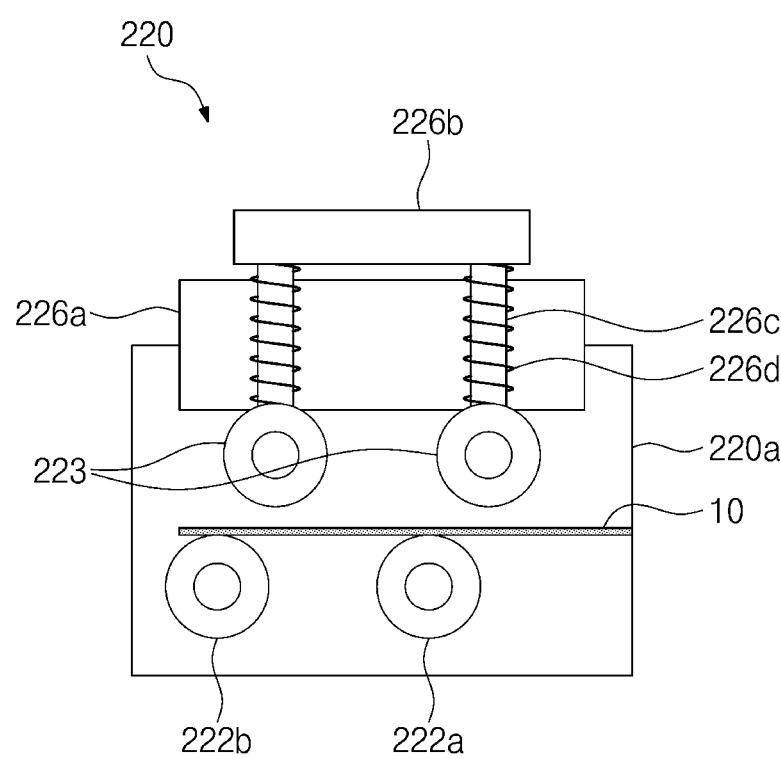

[FIG. 14]
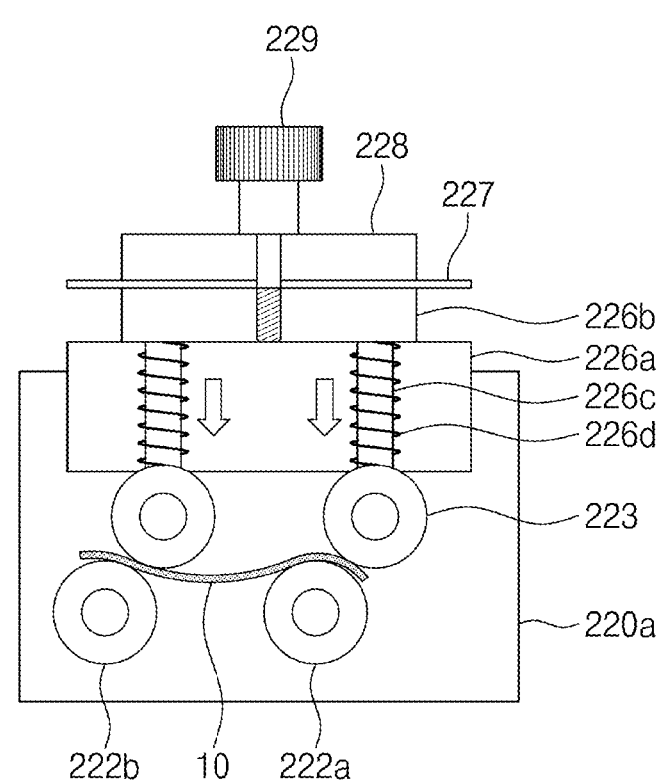

[FIG. 15]

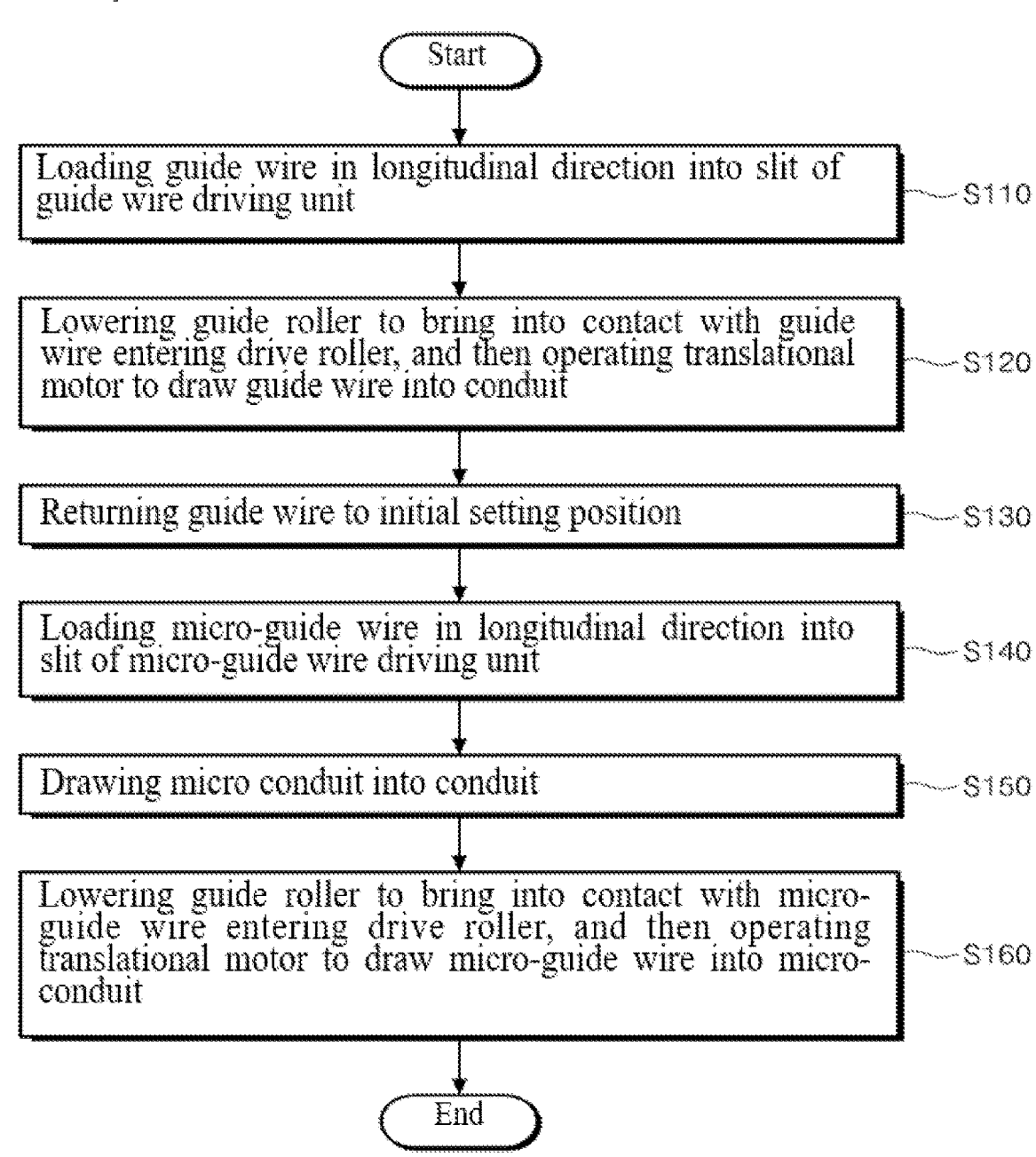

Start

Loading guide wire in longitudinal direction into slit of guide wire driving unit ~ S110

Lowering guide roller to bring into contact with guide wire entering drive roller, and then operating translational motor to draw guide wire into conduit ~ S120

Returning guide wire to initial setting position ~ S130

Loading micro-guide wire in longitudinal direction into slit of micro-guide wire driving unit ~ S140

Drawing micro conduit into conduit ~ S150

Lowering guide roller to bring into contact with micro-guide wire entering drive roller, and then operating translational motor to draw micro-guide wire into micro-conduit ~ S160

End

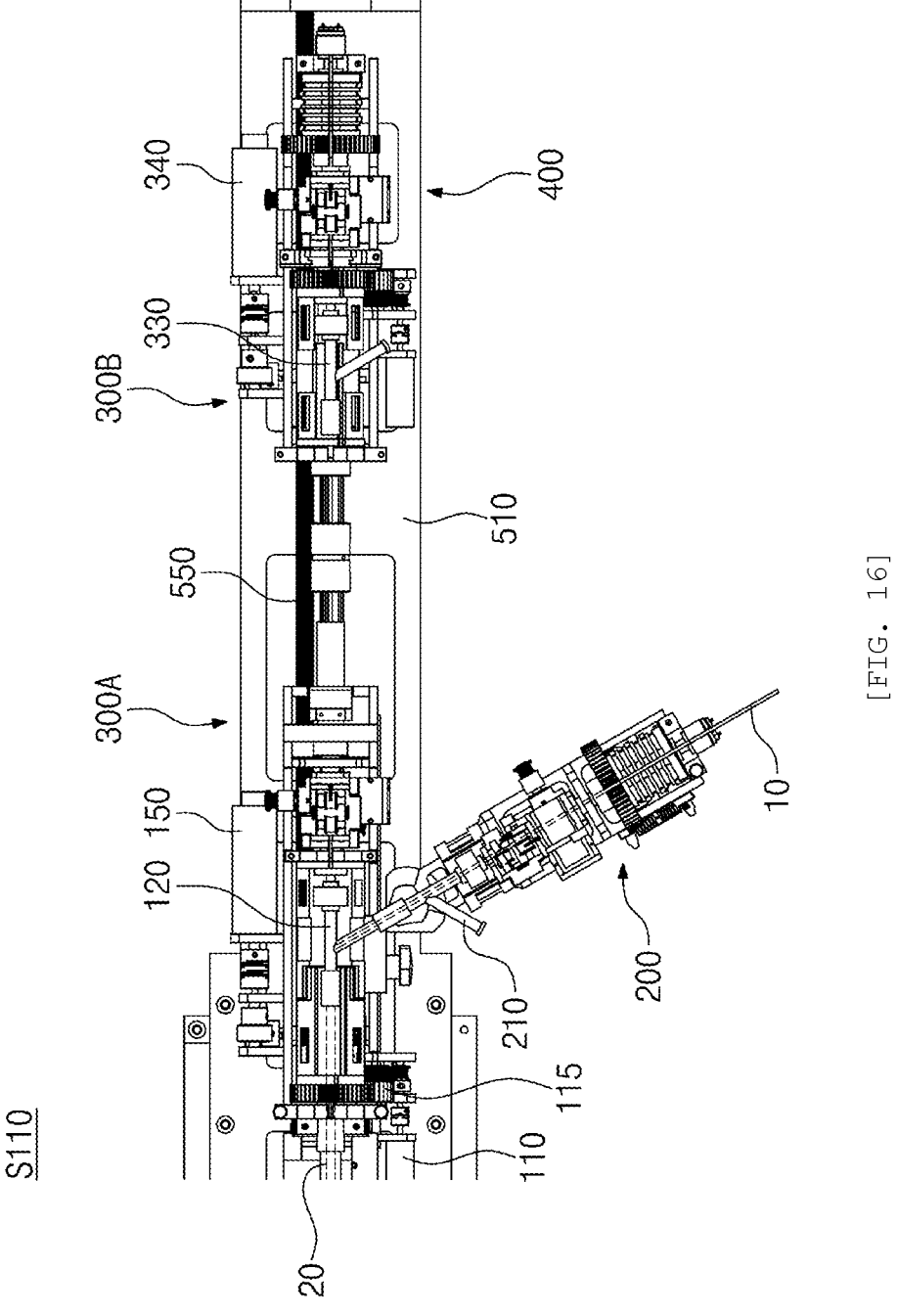
[FIG. 16]

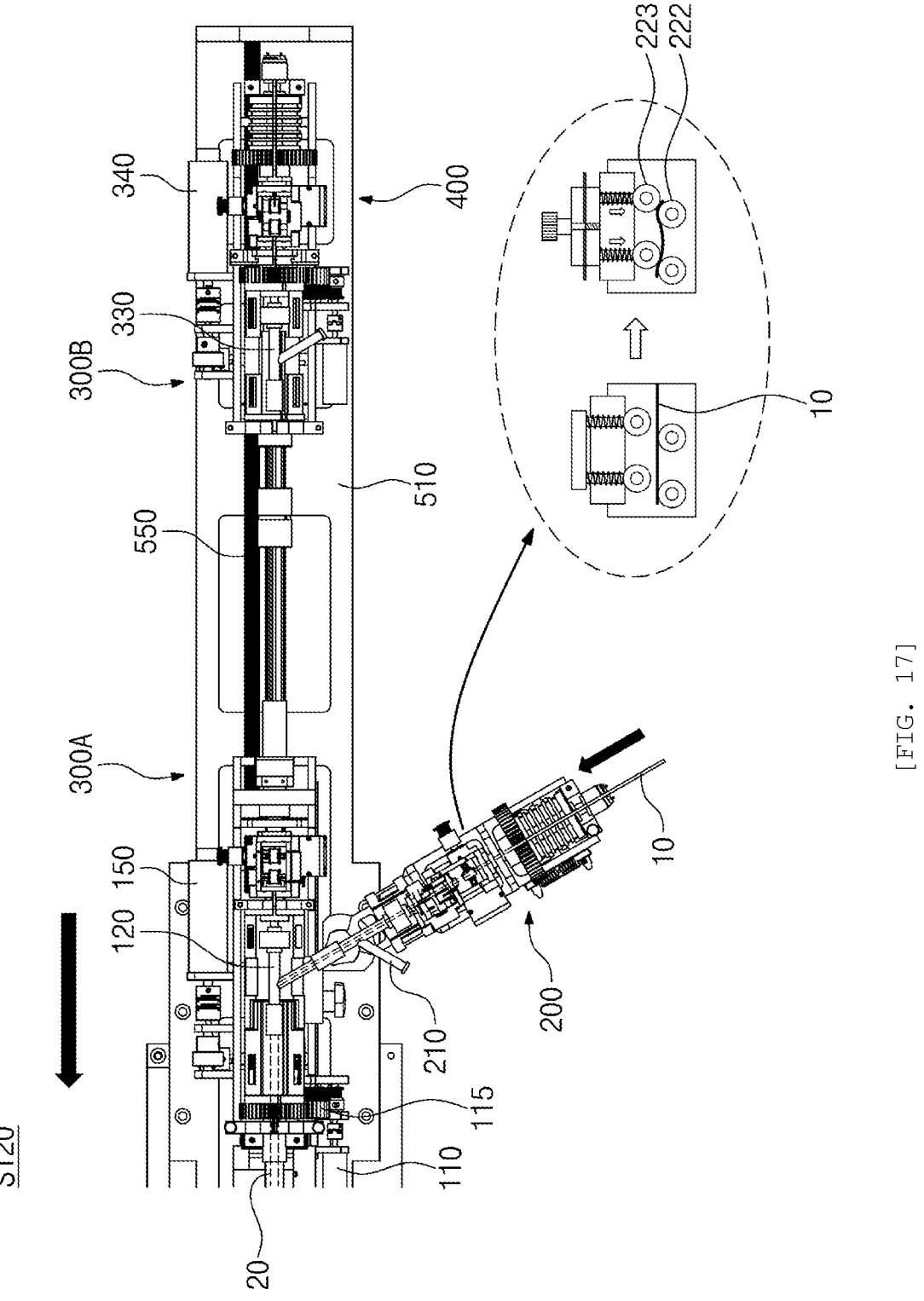
[FIG. 17]

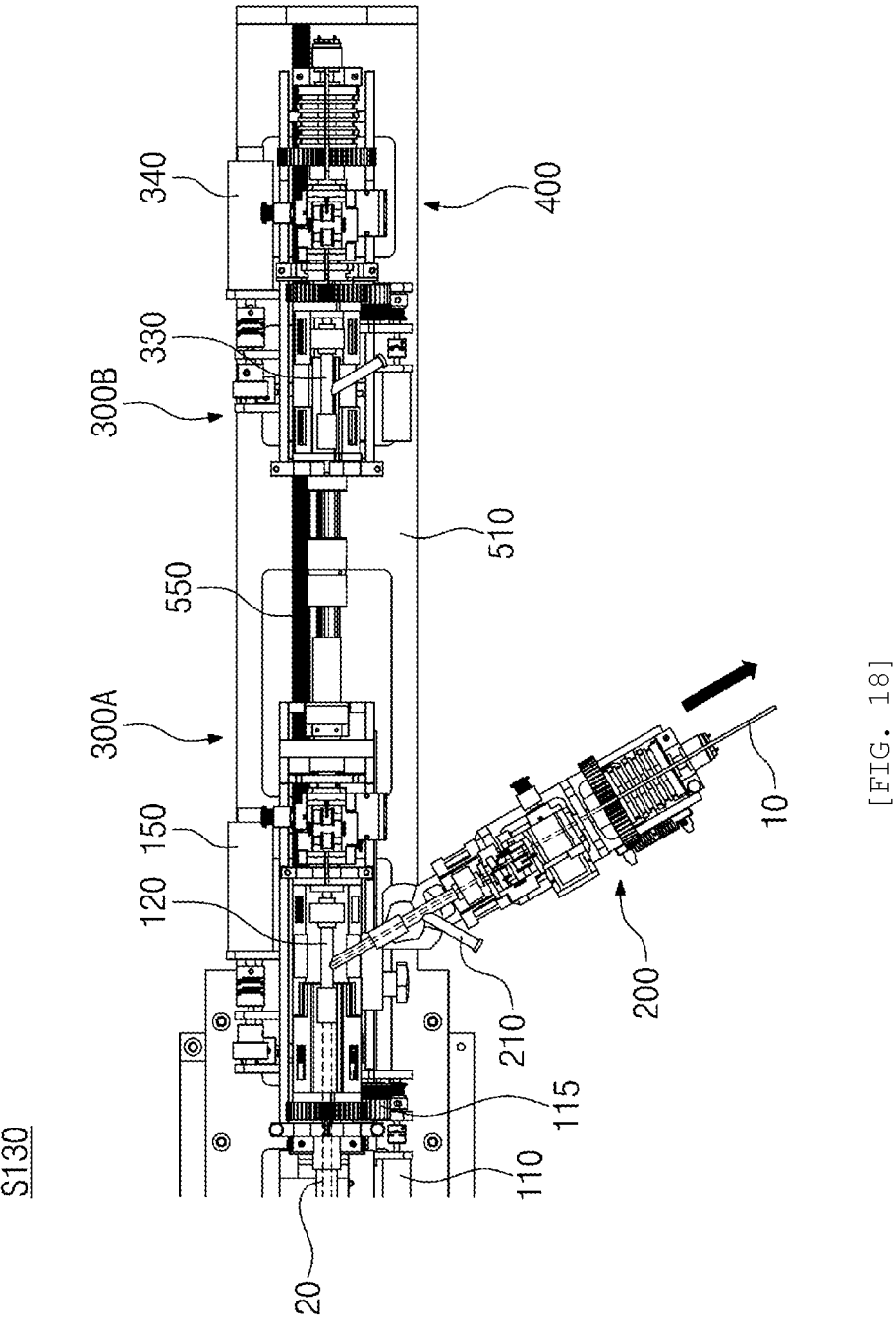
[FIG. 18]

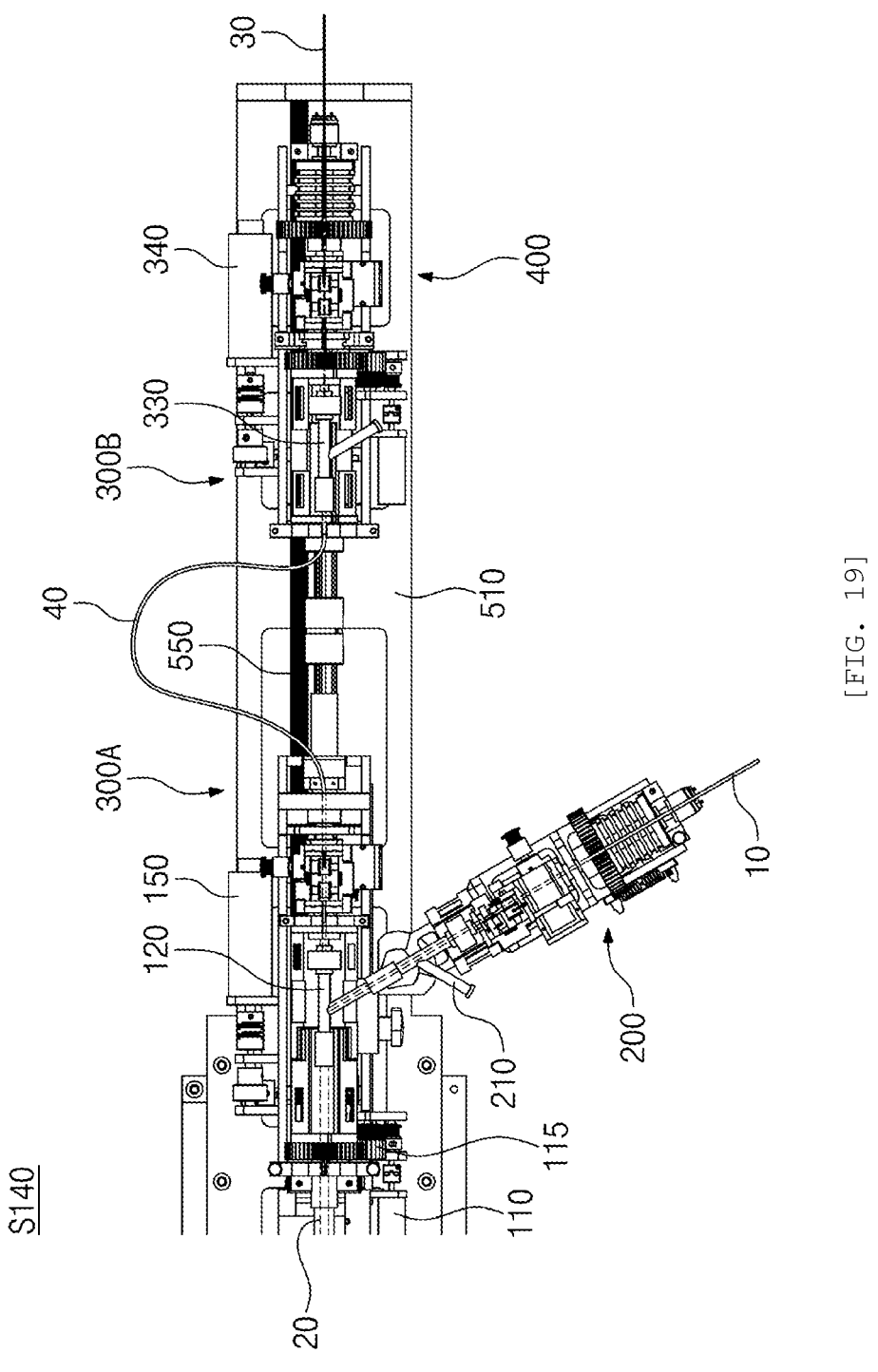
[FIG. 19]

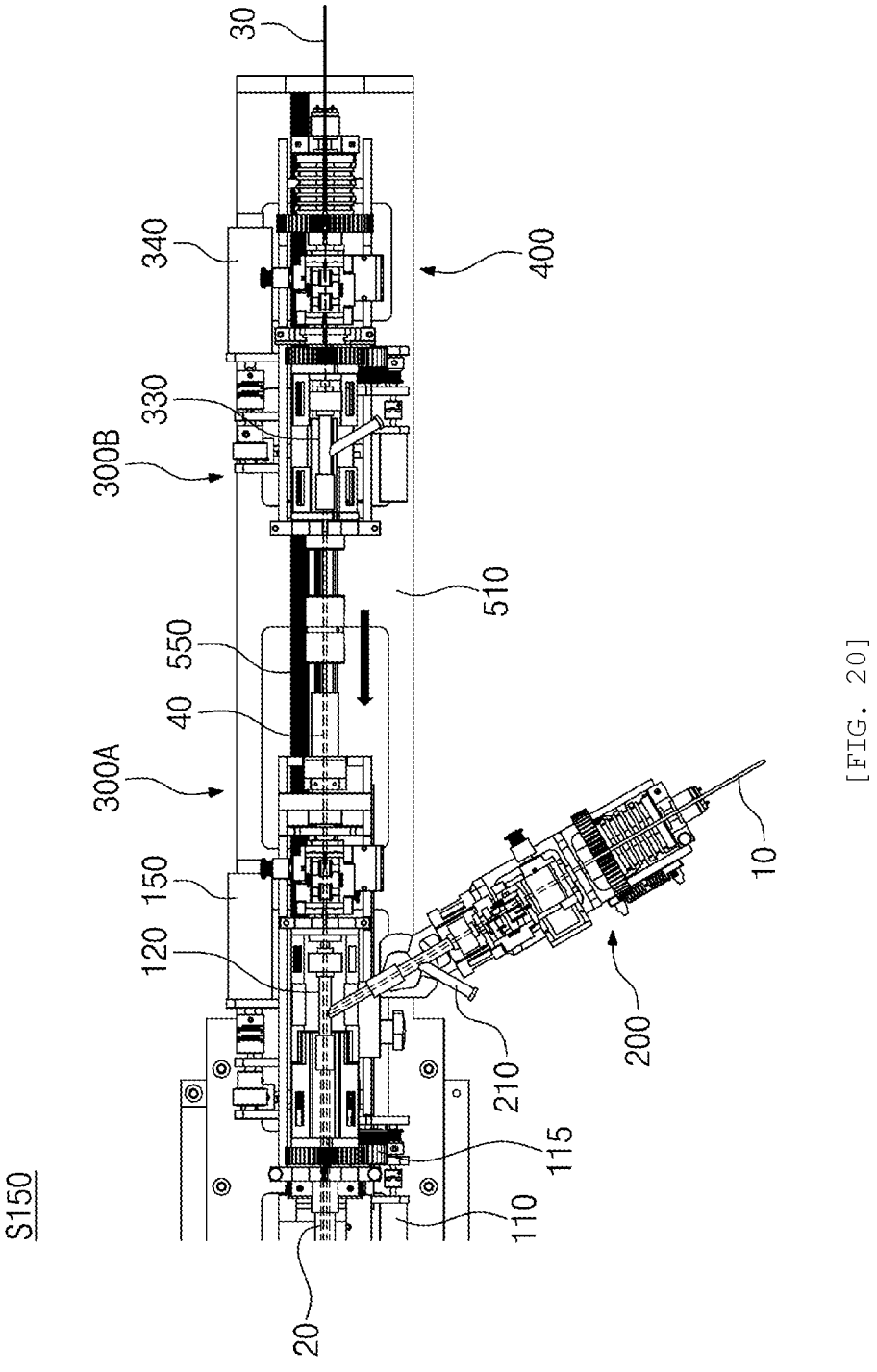
[FIG. 20]

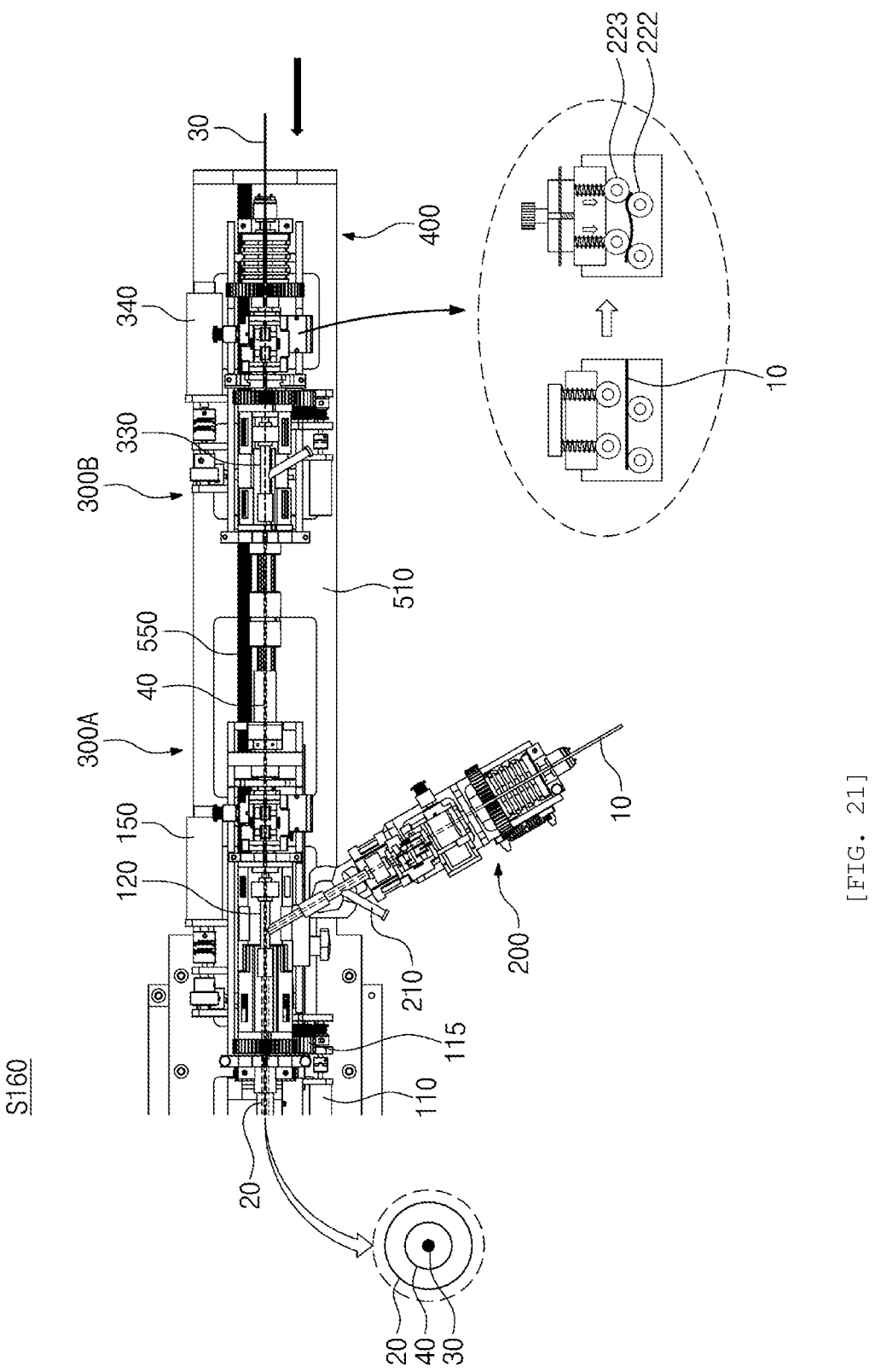
[FIG. 21]

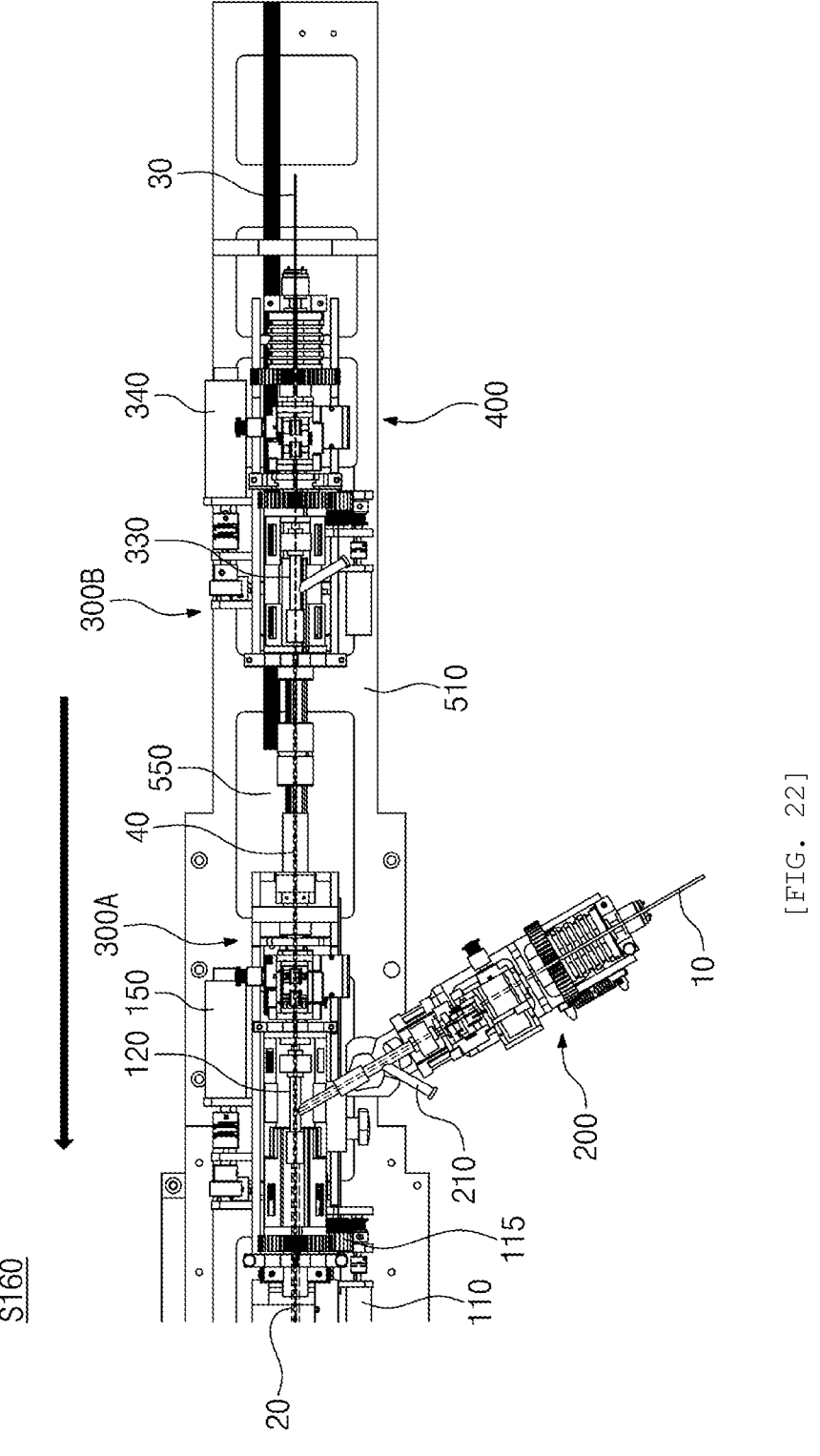
[FIG. 22]

VASCULAR INTERVENTION ROBOT AND VASCULAR INTERVENTION SYSTEM HAVING LINE-CONTACT ROLLER MECHANISM

CROSS-REFERENCE TO RELATED APPLICATIONS

This application is the U.S. National Phase under 35 U.S.C. § 371 of International Application No. PCT/KR2022/000962, filed on Jan. 19, 2022, which in turn claims the benefit of Korean Application No. 10-2021-0007643, filed on Jan. 19, 2021, the disclosures of which are incorporated by reference into the present application.

TECHNICAL FIELD

The present invention relates to a vascular intervention robot having a line-contact roller mechanism and a vascular intervention system, and more particularly, to a vascular intervention robot having a line-contact roller mechanism and a vascular intervention system to minimize slip of a medical wire translated by a roller.

BACKGROUND ART

Vascular intervention refers to a minimally invasive procedure for the treatment of vascular diseases or cancer, in which a thin conduit (catheter) having a diameter of several mm or less is inserted percutaneously through a blood vessel to a lesion site mainly under X-ray fluoroscopy to reach a target organ and treat the lesion. Representative treatments for the vascular intervention in Korea and other countries include trans-arterial chemoembolization (TACE) for liver cancer, percutaneous angioplasty, and artificial vascular stent installation in aortic diseases.

In particular, liver cancer is the main cause of death according to data from the National Cancer Information Center published in 2011, it was found that the incidence of liver cancer is the fifth highest entirely in men and women after stomach, thyroid, colon and lung, but death from liver cancer is the second highest entirely in men and women after lung cancer. The radical treatment of liver cancer is surgical resection, but most advanced liver cancer, which cannot be treated radically at the time of diagnosis, is treated with TACE.

Specifically, TACE refers to a treatment for finding an artery that supplies nutrition to a liver tumor and administering an anticancer agent, thereby blocking blood vessels (see FIG. 1). According to the sequence of procedure, the femoral artery positioned in the inguinal region (groin) is pierced with a needle and then a guide wire, a conduit (see FIG. 2) or the like is inserted through the pierced femoral artery so as to be approached to an upper part of the origin of the hepatic artery (see FIG. 3). Thereafter, a hepatic arteriogram is obtained while injecting an angioplasty agent to obtain information necessary for treatment, such as the location, size, and blood supply pattern of the tumor, thereby determining treatment schemes such as types, doses and the like of appropriate anticancer agents or embolic materials. When the treatment scheme is determined, a micro-catheter having a diameter of about 3 F (1 F=0.33 mm) is inserted into the origin to treat the tumor. The procedure time is generally about 1 to 2 hours, and the patient's hepatic artery branch pattern and the artery branch distribution of the tumor may vary depending on the complexity.

As shown in FIG. 4, most of the blood vessels are divided into several branches or formed in a curved shape. Thus, in the vascular intervention procedure, inserts having various stages in diameter, which are called co-axial systems of conduits and guide wires, are used in combination to prevent damages to the blood vessels. In addition, in the conventional vascular intervention procedure, a master-slave type system capable of remotely controlling surgical tools is used to reduce radiation exposure of an operator.

In the vascular intervention robot applied to the vascular intervention, the guide wire is translated by a roller mechanism and is drawn into a conduit.

In the conventional roller mechanism, the drive roller is rotated to translate the guide wire in a state in which a drive roller and a manual roller are disposed in a vertical direction and the drive roller is rotated while the drive roller and the manual roller come into point contact with the guide wire by pressing the guide wire introduced between the drive roller and the manual roller.

However, since the rollers simply come into point contact with the guide wire, that is, since a contact portion between the rollers and the guide wire is very narrow, the translating guide wire is frequently slipped on surfaces of the rollers when the roller mechanism is driven.

DISCLOSURE

Technical Problem

An object of the present invention is to provide a vascular intervention robot having a line-contact roller mechanism capable of minimizing slip of a medical wire translated by a roller.

Another object of the present invention is to provide a vascular intervention robot having a line-contact roller mechanism and a vascular intervention system including the same so as to improve convenience and stability of vascular intervention.

The technical problems to be solved by the present invention are not limited to those described above.

Technical Solution

In order to solve the above technical problem, the present invention provides a vascular intervention robot having a line-contact roller mechanism.

According to one embodiment, the vascular intervention robot having a line-contact roller mechanism includes: a roller module for translating a medical wire; and a rotational module for rotating the roller module to axially rotate the medical wire, wherein the roller module includes: a translational motor for providing a translational driving force for translating the medical wire; at least one drive roller receiving the translational driving force from the translational motor, arranged in a longitudinal direction of the medical wire, and coming into rolling contact with a lower side of the medical wire; and a plurality of guide rollers provided in a number corresponding to a number of the drive roller and arranged on the drive roller in the longitudinal direction of the medical wire, so as to be shifted to one side in the longitudinal direction of the medical wire with respect to the drive roller and coming into rolling contact with an upper side of the medical wire.

According to one embodiment, the drive roller and the guide roller may have an overlapping region partially overlapping in a vertical direction, and the medical wire positioned between the drive roller and the guide roller may come into line contact with the drive roller and the guide roller in the overlapping region.

According to one embodiment, the medical wire may be moved in a curved line to have a sine wave form and passes through the roller module.

According to one embodiment, the drive roller may include a first drive roller and a second drive roller, and the roller module may further include a belt pulley, in which the belt pulley connects the first drive roller to the translational motor, and the second drive roller is interlocked with rotation of the first drive roller.

According to one embodiment, the roller module may include: a driving gear coupled to a rotational shaft of the first drive roller; a driven gear coupled to a rotational shaft of the second drive roller; and an idle gear gear-coupled between the driving gear and the driven gear to rotate the driven gear in a same direction as a rotation direction of the driving gear.

According to one embodiment, the roller module may further include a housing for accommodating the drive roller and the guide roller, and an elevating unit installed in the housing to elevate the guide roller in a vertical direction with respect to the drive roller, and the elevation unit may vertically lower the guide roller to guide a translational motion of the medical wire while the guide roller is rotated relative to the drive roller when the medical wire enters the drive roller.

According to one embodiment, the elevating unit may include: a base for supporting the guide roller above the guide roller; a roller fixing block spaced apart above the base; a roller shaft passing through the base and connecting the guide roller to the roller fixing block; and a spring member provided on an outer circumferential surface of the roller shaft in the longitudinal direction, and interlocked with a descending motion of the roller fixing block coming into close contact with the base to elastically press the guide roller downward so that the guide roller presses the medical wire.

According to one embodiment, the roller module may include: a hinge cover for opening and closing the housing and pressing the roller fixing block downward by a coupling force applied to the housing when the housing is closed; a knob fixing block provided on the hinge cover; and a bolt-type knob coupled to the knob fixing block to provide a pressing force to the spring member through the base while descending from the knob fixing block when being rotated.

According to one embodiment, the medical wire may include any one of a guide wire drawn into a conduit inserted into a human body and a micro-guide wire drawn into a micro-conduit drawn into the conduit.

According to one embodiment, the vascular intervention robot further includes: a conduit driving unit, wherein the conduit driving unit rotates and translates the conduit extending in the longitudinal direction around the longitudinal direction as an axis.

According to one embodiment, the guide wire may be translated into the conduit by the roller module, and rotated coaxially to the conduit by rotation of the roller module by the rotational module.

According to one embodiment, the vascular intervention robot may further include: a micro-conduit driving unit, wherein the micro-conduit driving unit is provided at a rear side of the conduit driving unit to translate the micro-conduit along a path coaxial to the conduit and different from a path through which the guide wire is drawn in and out with respect to the conduit when the guide wire is drawn out from the inside of the conduit.

According to one embodiment, the micro-guide wire may be translated toward the inside of the micro-conduit by the roller module, and rotated coaxially to the micro-conduit by rotation of the roller module by the rotational module.

Meanwhile, the present invention provides a vascular intervention system.

According to one embodiment, the vascular intervention system includes: a vascular intervention robot of claim 1; and a frame fixing the vascular intervention robot so as to be movable relative to a surgical bed.

Advantageous Effects

According to one embodiment, the vascular intervention robot having a line-contact roller mechanism includes: a roller module for translating a medical wire; and a rotational module for rotating the roller module to axially rotate the medical wire, wherein the roller module includes: a translational motor for providing a translational driving force for translating the medical wire; at least one drive roller receiving the translational driving force from the translational motor, arranged in a longitudinal direction of the medical wire, and coming into rolling contact with a lower side of the medical wire; and a plurality of guide rollers provided in a number corresponding to a number of the drive roller and arranged on the drive roller in the longitudinal direction of the medical wire, so as to be shifted to one side in the longitudinal direction of the medical wire with respect to the drive roller and coming into rolling contact with an upper side of the medical wire.

Therefore, the present invention provides the vascular intervention robot having a line-contact roller mechanism, so that slip of the medical wire can be minimized when the medical wire is axially rotated in accordance with the rotation of the roller module due to the rotation module In addition, the present invention provides the vascular intervention robot having a line-contact roller mechanism, so that slip of the medical wire translated by means of the roller can be minimized on the surface of the roller.

In other words, according to one embodiment of the present invention, the vascular intervention robot having a line-contact roller mechanism is provided, so that slip of a rotating and translating medical wire can be minimized.

Therefore, according to one embodiment of the present invention, the vascular intervention system is provided, so that convenience and stability of vascular intervention procedure can be improved and time for the procedure can be reduced.

DESCRIPTION OF DRAWINGS

FIG. 1 is a schematic diagram showing hepatic cancer and a nutrient-fed hepatic artery.

FIG. 2 is a photograph showing a conduit (left) and a micro-conduit-induced iron wire assembly (right) used in a TACE procedure.

FIG. 3 is a schematic view of a procedure showing an insertion conduit having a diameter of 6-7 F on the outside and a state in which a guide wire having a diameter of 3-4 F is rotatably inserted in the insertion conduit.

FIG. 4 is a photograph showing an example of hepatic artery chemoembolization.

FIG. 5 is a view for explaining a vascular intervention system using a vascular intervention robot according to one embodiment of the present invention.

FIG. 6 is a perspective view showing the vascular intervention robot according to the one embodiment of the present invention.

FIG. 7 is a view showing an arrangement state of a conduit, a guide wire, and a micro-conduit when a front end of the guide wire returns to an initial setting position in the vascular intervention robot according to the one embodiment of the present invention.

FIG. 8 is a perspective view showing a guide wire driving unit of the vascular intervention robot according to the one embodiment of the present invention.

FIG. 9 is one side view showing a roller module of a guide wire driving unit according to an exemplary embodiment of the present invention.

FIG. 10 is another side view showing the roller module of the guide wire driving unit according to an exemplary embodiment of the present invention.

FIG. 11 is a sectional view showing the roller module of the guide wire driving unit according to an exemplary embodiment of the present invention.

FIG. 12 is a schematic view schematically showing the roller module of the guide wire driving unit according to an exemplary embodiment of the present invention when viewed from above.

FIGS. 13 and 14 are schematic views for explaining operations of the roller module according to one embodiment of the present invention.

FIG. 15 is a flowchart sequentially illustrating a method of driving the vascular intervention robot according to one embodiment of the present invention.

FIGS. 16 to 22 are reference views for explaining step of the method of driving the vascular intervention robot according to one embodiment of the present invention.

BEST MODE

Mode for Invention

Hereinafter, preferred embodiments of the present invention will be described in detail with reference to the accompanying drawings. However, the technical idea of the present invention is not limited to the exemplary embodiments described herein and may be embodied in other forms. Further, the embodiments are provided to enable contents disclosed herein to be thorough and complete and provided to enable those skilled in the art to fully understand the idea of the present invention.

Herein, when one component is mentioned as being on other component, it signifies that the one component may be placed directly on the other component or a third component may be interposed therebetween. In addition, in the drawings, shapes and sizes may be exaggerated to effectively describe the technical content of the present invention.

In addition, although terms such as first, second and third are used to describe various components in various embodiments of the present specification, the components will not be limited by the terms. The above terms are used merely to distinguish one component from another. Accordingly, a first component referred to in one embodiment may be referred to as a second component in another embodiment. Each embodiment described and illustrated herein may also include a complementary embodiment. In addition, the term "and/or" is used herein to include at least one of the components listed before and after the term.

The singular expression herein includes a plural expression unless the context clearly specifies otherwise. In addition, it will be understood that the term such as "include" or "have" herein is intended to designate the presence of feature, number, step, component, or a combination thereof recited in the specification, and does not preclude the possibility of the presence or addition of one or more other features, numbers, steps, components, or combinations thereof. In addition, the term "connection" is used herein to include both indirectly connecting a plurality of components and directly connecting the components.

In addition, in the following description of the embodiments of the present invention, the detailed description of known functions and configurations incorporated herein will be omitted when it possibly makes the subject matter of the present invention unclear unnecessarily.

FIGS. 5 to 14 are views showing a vascular intervention robot according to one embodiment of the present invention.

As shown in FIG. 5, a vascular intervention robot 1000 according to one embodiment of the present invention may be applied to a vascular intervention system composed of a remote procedure system based on master-slave device. According to the vascular intervention system, an operator remotely controls the procedure on a master device side, and a slave device performs the procedure on the patient according to the remote control. Accordingly, the present invention may minimize an environment in which the operator is exposed to radiation.

First, the vascular intervention system will be briefly described. The vascular intervention system may further include a bed 1100, a frame 1200 and a master device 1300 in addition to the vascular intervention robot 1000 according to one embodiment of the present invention.

The bed 1100 provides a procedure surface on which a patient 1120 is allowed to lie, so that the patient may receive the procedure while lying down. The frame 1200 may be movably attached to the bed 1100. One side of the frame 1200 may accommodate and fix the vascular intervention robot 1000.

For example, the vascular intervention robot 1000 may be mounted on an upper side of the frame 1200. The vascular intervention robot 1000 may be mounted to be rotatable or translatable with respect to the frame 1200. The other side of the frame 1200 may be attached to the bed 1100 so as to be movable.

For example, the other side of the frame 1200 may be movably attached to a rail of the bed 1100. As described above, the vascular intervention robot 1000 is provided to be rotatable and translatable with respect to the frame 1200, so that convenience of the procedure may be improved.

Meanwhile, the master device 1300 may provide an interface for enabling an operator 1110 to remotely control the vascular intervention robot 1000. As described above, the operator 1110 may remotely control the vascular intervention robot 1000, so that radiation exposure on the operator may be minimized.

As shown in FIGS. 6 and 7, the vascular intervention robot 1000 according to one embodiment of the present invention applied to the vascular intervention system may include a conduit driving unit 100, a guide wire driving unit 200, a micro-conduit driving unit 300, and a micro-guide wire driving unit 400.

In addition, the vascular intervention robot 1000 according to one embodiment of the present invention may further include a transfer unit 500 and a conduit guide unit 600.

The vascular intervention robot 1000 according to one embodiment of the present invention may have a line-contact roller mechanism for a medical wire.

In one embodiment of the present invention, the line-contact roller mechanism may be applied to the guide wire driving unit 200 for driving the guide wire 10 used as a medical wire.

In addition, in one embodiment of the present invention, the line-contact roller mechanism may be applied to the micro-guide wire driver 400 driving the micro-guide wire 30 used as a medical wire.

The line-contact roller mechanism may be implemented through roller modules 220 and 420, which will be described later in more detail.

The roller module 220 for implementing the line-contact roller mechanism applied to the guide wire driving unit 200 and the roller module 420 for implementing the line-contact roller mechanism applied to the micro-guide wire driving unit 400 have the same configuration as each other, except for the object to be driven, and accordingly, may perform the same role, function, and action.

The conduit driving unit 100 may rotate and translate a conduit 20 extending in the longitudinal direction around a longitudinal axis. Accordingly, the conduit driving unit 100 may insert the conduit 20 into a target blood vessel. The conduit driving unit 100 may rotate the conduit while gripping the conduit 20.

For example, when the conduit 20 encounters a curved portion of a blood vessel, the conduit driving unit 100 may rotate the conduit 20 about the longitudinal axis of the conduit 20 in order to change the direction of a front end thereof. To this end, the conduit driving unit 100 may include a conduit rotation driving body 110 and a gear 115.

The conduit rotation driving body 110 refers to a device for providing a rotational driving force for rotating the conduit 20, and may be provided as, for example, a motor.

The gear 115 may receive a rotational driving force from the conduit rotation driving body 110 to provide the rotational force for rotating the conduit 20. The gear 115 may be provided with a slit through which the conduit 20 may be loaded in the axial direction of the gear 115.

Referring to FIG. 7, the conduit driving unit 100 may further include a first Y-shaped connector 120. The first Y-shaped connector 120 provides a connection path between the conduit 20 and the guide wire 10 and between the conduit 20 and the micro-conduit 40.

To this end, the first Y-shaped connector 120 may include a main body 123 and a branch portion 125.

The main body 123 may have a tubular shape in which the inside thereof has a hollow. The main body 123 may have an opened longitudinal one end so that the conduit 20 may be inserted thereto and gripped.

In addition, the main body 123 may have a longitudinal other end connected to the micro-conduit driving unit 300. Accordingly, a longitudinal front end of the micro-conduit 40 may be positioned at the longitudinal other end of the main body 123.

However, in an initial setting for inserting the conduit 20 and the guide wire 10 into the target blood vessel, the micro-conduit 40 is not mounted in the micro-conduit driving unit 300. Accordingly, in the initial setting, the longitudinal front end of the micro-conduit is not positioned at the longitudinal other end of the main body 123.

Like the main body 123, the branch portion 125 may have a tubular shape in which the inside has a hollow. The branch portion 125 may be formed to branch from one side of the main body 123 in the longitudinal direction. The hollow of the branch portion 125 may communicate with the hollow of the main body 123.

In an exemplary embodiment of the present invention, the guide wire driving unit 200 configured to rotate and translate the guide wire may be connected to a longitudinal end of the branch portion 125.

In the initial setting for inserting the conduit 20 and the guide wire 10 into the target blood vessel, a rear end of the conduit 20 in the longitudinal direction may be inserted and gripped into one end of the main body 123 in the longitudinal direction, and the front end of the guide wire 10 may be disposed at a branch point side of the branch portion 125.

Thereafter, when the vascular intervention robot 1000 is operated and the guide wire 10 and the conduit 20 are inserted into the target blood vessel, the guide wire 10 is moved rearward and the front end thereof is returned to the initial setting position. As described above, when the front end of the guide wire 10 returns to the initial setting position, the micro-conduit 40 may be mounted in the micro-conduit driving unit 300. Accordingly, the front end of the micro-conduit 40 is positioned at the other end of the main body 123 in the longitudinal direction.

Accordingly, when the micro-conduit 40 is drawn into the conduit 20, the micro-conduit 40 may be drawn in and out through a path different from the draw-in-and-out path of the guide wire 10 with respect to the conduit 20.

According to one embodiment of the present invention, the micro-conduit 40 may be drawn in and out coaxially with respect to the conduit 20. Accordingly, when the micro-conduit 40 is inserted into the conduit 20, the guide wire 10 is prevented from being interfered with the draw-in-and-out, and as a result, the convenience of the vascular intervention procedure may be improved and the procedure time may be shortened.

The first Y-shaped connector 120 may be seated in the case 133. A cover 135 may be coupled to an upper side of the case 133.

The cover 135 may be coupled to the case 133 while covering the first Y-shaped connector 120. The case 133 and the cover 135 serve to protect the first Y-shaped connector 120 from an external environment.

Meanwhile, the conduit driving unit 100 may translate the conduit such that the conduit 20 is inserted to the target blood vessel. To this end, the conduit driving unit 100 may further include a conduit translational driving body 150.

The conduit translational driving body 150 provides a driving force to a rack 550 and a pinion 560 provided in the transfer unit 50, and moves the conduit driving unit 100 mounted in the assembly of the rack 550 and the pinion 560. The conduit 20 is translated through the movement of the conduit driving unit 100.

According to one embodiment of the present invention, the guide wire driving unit 200 may be provided at a lateral side of the conduit driving unit 100. The guide wire driving unit 200 translates the guide wire 10 to draw the guide wire 10 into the conduit 20 and insert the guide wire 10 up to the vicinity of the target vessel, and rotates the guide wire 10 coaxially with the conduit 20.

The guide wire driving unit 200 is connected to the branch portion 125 of the first Y-shaped connector 120. To this end, the guide wire driving unit 200 may include a second Y-shaped connector 210 serving as a connection means and coupled to the branches 125 of the first Y-shaped connector 120.

The second Y-shaped connector 210 may have the same structure as the first Y-shaped connector 120.

Accordingly, the guide wire driving unit 200 may provide the guide wire 10 into the conduit 20 drawn in and grasped at the longitudinal one end of the main body 123 through the second Y-shaped connector 210 and the branch portion 125 of the first Y-shaped connector 120.

The guide wire driving unit 200 may include a roller module 220 for implementing a line-contact roller mechanism and a rotational module 230 for rotating the roller module 220 to axially rotate the guide wire 10.

Referring to FIGS. 8 to 11, the roller module 220 may translate the guide wire 10 used as a medical wire.

According to one embodiment of the present invention, the roller module 220 may include a housing 220a, a translational motor 221, a drive roller 222, and a guide roller 223.

The housing 220a defines an appearance of the roller module 220. The housing 220a provides a mounting space for the translational motor 221, the drive roller 222, and the guide roller 223 so as to be mounted therein, and protects the above components from an external environment. An inner space of the housing 220a in which the drive roller 222 and the guide roller 223 are mounted and an inner space of the housing 220a in which the translational motor 221 is mounted may be spatially separated from each other.

Meanwhile, a hinge cover 227 configured to open or close an internal space of the housing 220a may be installed at an upper end of the housing.

The translational motor 221 may be mounted in one side of the inner space of the housing 220a. The translational motor 221 may be disposed below the drive roller 222. The translational motor 221 may provide a translational driving force for translating the guide wire to the drive roller 222.

The drive roller 222 may be rotated by receiving the translational driving force from the translational motor 221. The drive roller 222 may come into rolling contact with a lower side of the guide wire 10. Accordingly, when the drive roller 222 is rotated, the guide wire 10 may be translated by the drive roller 222.

At least one drive roller 222 may be provided. The drive roller 222 according to one embodiment of the present invention may include a first drive roller 222a and a second drive roller 222b. The first drive roller 222a and the second drive roller 222b may be arranged in the longitudinal direction of the guide wire 10.

A rotational shaft of the first drive roller 222a and a rotational shaft of the translational motor 221 may be connected to each other through a belt pulley 224. Accordingly, when the rotational shaft of the translational motor 221 is rotated, the rotational shaft of the first drive roller 222a is also rotated.

The second drive roller 222b may be interworked with the rotation of the first drive roller 222a that receives rotational force from the translational motor 221.

To this end, the roller module 220 according to one embodiment of the present invention may include a driving gear 225a, a driven gear 225b, and an idle gear 255c.

The driving gear 225a may be coupled to the rotational shaft of the first drive roller 222a. When the belt pulley 224 is connected to one side of the first drive roller 222a in the longitudinal direction of the rotational shaft, driving gear may be connected to the other side of the first drive roller 222a in the longitudinal direction of the rotational shaft.

The driven gear 225b may be coupled to the rotational shaft of the second drive roller 222b. The driven gear 225b may be laterally arranged in parallel with the driving gear 225a.

The idle gear 225c may be engaged between the driving gear 225a and the driven gear 225b. Due to the idle gear 225c, the rotational force of the driving gear 225a is transferred to the driven gear 225b and rotates the driven gear in the same direction.

When the rotational shaft of the translational motor 221 is rotated in the clockwise direction, the rotational shaft of the first drive roller 222a is also rotated in the clockwise direction. Accordingly, the driving gear 225a is rotated in the clockwise direction. Accordingly, the idle gear 225c gear-coupled to the driving gear 225a is rotated in the counter-clockwise direction, and the driven gear 225b gear-coupled to the idle gear 225c is rotated in the clockwise direction, that is, in the same direction as the driving gear 225a by the counterclockwise rotation of the idle gear 225c. Accordingly, the second drive roller 222b axially coupled to the driving gear 225a is also rotated in the same direction as the first drive roller 222a, and accordingly, the guide wire 10 coming into rolling contact with the first drive roller 222a and the second drive roller 222b may be translated in one direction.

The guide roller 223 may be disposed over the drive roller 222. The guide roller 223 may be provided in a number corresponding to the drive roller 222. In one embodiment of the present invention, the drive roller 222 may include a first drive roller 222a and a second drive roller 222b. Accordingly, the guide roller 223 may be provided as two rollers corresponding the first and second drive rollers so as to be arranged in the longitudinal direction of the guide wire 10.

The guide roller 223 comes into rolling contact with an upper side of the guide wire 10 positioned on the drive roller 222, and guides the translational motion of the guide wire 10 while being rotated relative to the drive roller 222.

According to one embodiment of the present invention, the guide roller 223 may be shifted to one side of the guide wire 10 in the longitudinal direction with respect to the drive roller 222.

In other words, referring to FIG. 11, when a vertical central axis of the drive roller 222 is called "A", the guide roller 223 has a vertical central axis "B" shifted to one side from the vertical central axis "A" of the drive roller 222.

Referring to FIG. 12, accordingly, the drive roller 222 and the guide roller 223 have an overlapping region "C" partially overlapping with each other in the vertical direction. As a result, the guide wire positioned between the drive roller 222 and the guide roller 223 comes into line contact with the drive roller 222 and the guide roller 223 in the overlapping region "C".

In the related art, the drive roller and the guide roller are vertically arranged. Accordingly, when the guide wire 10 is positioned therebetween, upper and lower sides of the guide wire 10 come into point contact with the rollers, respectively. Due to the narrow contact part, the guide wire 10 is frequently slipped on the drive roller.

On the contrary, according to one exemplary embodiment of the present invention, when the guide roller 223 is shifted to one side in the longitudinal direction of the guide wire 10 on the drive roller 222, and the drive roller 222 and the guide roller 223 have the overlapping region "C" partially overlapping in the vertical direction, the guide wire 10 positioned between the drive roller 222 and the guide roller 223 comes into line contact therebetween. Due to an increase in the contact part, the phenomenon, in which the guide wire 10 is slipped on the drive roller 222, may be minimized.

In other words, according to one embodiment of the present invention, the guide wire 10 passing between the drive roller 222 and the guide roller 223 may be translated while being stably supported by the drive roller 222 and the guide roller 223.

As the guide roller 223 is shifted on the drive roller 222 to the one side in the longitudinal direction of the guide wire 10, the guide wire 10 passes through the roller module 220, that is, between the drive roller 222 and the guide roller 223 while curving, for example, in a sine wave faint.

Meanwhile, referring to FIG. 13, the guide roller 223 is positioned over the drive roller 222 so as to be spaced apart therefrom before the roller module 220 is driven.

As shown in FIG. 14, the guide roller 223 is required to be lowered toward the drive roller 222 in order to guide the translational motion of the guide wire 10 while being rotated relative to the drive roller 222.

To this end, the roller module 220 according to one embodiment of the present invention may further include an elevating unit 226.

The elevating unit 226 refers to a device for elevating the guide roller 223 in the vertical direction with respect to the drive roller 222, and may be installed in the housing 220*a*.

When the guide wire 10 enters the drive roller 222, the elevating unit 226 may vertically lower the guide roller 223 such that the guide roller 223 is rotated relative to the drive roller 222 to guide the translational motion of the guide wire 10, that is, come into contact with the upper side of the guide wire 10.

According to one embodiment of the present invention, the elevating unit 226 may include a base 226*a*, a roller fixing block 226*b*, a roller shaft 226*c*, and a spring member 226*d*.

The base 226*a* may be disposed above the guide roller 223. The base 226*a* serves to support the guide roller 223.

The roller fixing block 226*b* may be disposed above the base 226*a*. The roller fixing block 226*b* may be spaced apart from the base 226*a*.

The roller shaft 226*c* may have longitudinal one side connected to the guide roller 223 and the longitudinal other side fixed to the roller fixing block 226*b*. The roller shaft 226*c* may be disposed to pass through the base 226*a*. As such, the roller shaft 226*c* may connect the guide roller 223 to the roller fixing block 226*b*.

The spring member 226*d* may be provided on an outer circumferential surface of the roller shaft 226*c* in the longitudinal direction. The spring member 226*d* may be interlocked with a descending operation in which the roller fixing block 226*b* comes into close contact with the base 226*a*. Accordingly, the spring member 226*d* may elastically press the guide roller 223 downward.

The guide roller 223 may press the guide wire 10 with a constant pressure by the spring member 226*d*.

The roller module 220 according to one embodiment of the present invention may further include the hinge cover 227. The hinge cover 227 may be installed on the upper end of the housing 220*a* to open and close the housing 220*a*. When the hinge cover 227 closes the housing 220*a*, the roller fixing block 226*b* may be pressed downward by a coupling force applied to the housing 220*a*. In other words, as described above, the descending operation of allowing the roller fixing block 226*b* to come into close contact with the base 226*a* may occur by the fastening operation of the hinge cover 227 that closes the open upper end of the housing 220*a*.

Meanwhile, the roller module 220 may further include a knob fixing block 228 and a bolt-type knob 229. The knob fixing block 228 refers to a member for fixing the bolt-type knob 229 on the hinge cover 227.

The bolt-type knob 229 may be coupled to the knob fixing block 228. The bolt-type knob 229 may be rotated by an external force. As described above, when the bolt-type knob

229 is rotated, the bolt-type knob 229 presses the base 226*a* while descending from the knob fixing block 228. Accordingly, the bolt-type knob 229 may provide a pressing force to the spring member 226*d* through the base 226*a*.

In other words, according to one embodiment of the present invention, the lowering of the guide roller 223 for guiding the guide wire 10 may be induced by the fastening operation of the hinge cover 227 that closes the housing 220*a*. In addition, an additional pressing force may be provided to the guide roller 223 by an operation of rotating downward the bolt-type knob 229 in a state in which the guide roller 223 is lowered. Accordingly, the guide roller 223 may more stably guide the translational motion of the guide wire 10.

Referring back to FIG. 8, the rotational module 230 axially rotates the guide wire 10. To this end, the rotational module 230 rotates the roller module 220. In other words, the roller module 220 is rotated by the rotational module 230, and the guide wire 10 is axially rotated by the rotation of the roller module 220.

According to an exemplary embodiment of the present invention, the line contact of the guide wire 10 positioned between the drive roller 222 and the guide roller 223 may minimize the phenomenon in which the guide wire 10 is slipped on the drive roller 222 when guide wire 10 is axially rotated subject to the rotation of the roller module 220 by the rotational module 230.

In other words, according to an exemplary embodiment of the present invention, the guide wire 10 positioned between the drive roller 222 and the guide roller 223 comes into line contact therewith, so that the slip of the rotating and translating guide wire 10 can be minimized.

The rotational module 230 may include a rotational motor 237 and a rotational gear 236. The rotational motor 237 may provide a driving force for axially rotating the guide wire 10. The rotational gear 236 receives the driving force from the rotational motor 237.

To this end, the rotational gear 236 may be axially coupled to the rotary shaft of the rotational motor 237. The rotational gear 236 may be coaxially connected to the roller module 220, and accordingly, the rotational driving force provided from the rotational motor 237 may be transferred to the roller module 220 through the rotational gear 236.

A slit may be formed in the rotational gear 236. The slit may be formed at the same position in a circumferential direction as a slit 230*a* of at least one connection plate 231 described later.

Accordingly, the slit of the rotational gear 236 and the slits 230*a* of the at least one connection plate 231 foam a trench communicating in one direction, and the guide wire 10 may be loaded in the trench in the longitudinal direction.

When the roller module 220 is rotated by the rotational module 230, the translational motor 221 is also rotated. A plurality of electric lines (not shown) for driving the translational motor 221 are connected thereto, and the electric lines (not shown) may be twisted when the translational motor 221 is rotated.

When the twisting continues, an emergency may occur in which some or all of the electric lines (not shown) may be separated from the translational motor 221, and the operation of the vascular intervention robot 1000 is required to be stopped during the procedure.

In order to solve the above problem, the rotational module 230 according to one embodiment of the present invention may include a connection plate 231.

The connection plate 231 may be disposed behind the rotational gear 236. The connection plate 231 may be directly connected to the rotational gear 236. Accordingly, the connection plate 231 may be interlocked with the rotation of the rotational gear 236.

The number of the connection plate 231 may correspond to the electrical lines electrically connected between the translational motor 221 and the translational motor driver (not shown). In other words, each of the connection plates 231 may correspond to any one of the electrical lines (not shown).

The connection plates 231 may be arranged, behind the rotational gear 236, in one direction, for example, in the longitudinal direction of the guide wire 10.

Each of the connection plates 231 may be formed with a slit 230a opened in a central direction so as to use the guide wire 10 in the axial direction of the rotation of the roller module 220 by the rotational module 230. As described above, the slits 230a are connected to the slits of the rotational gear 236 to form a single trench structure.

A connection ring 232 may be disposed on the connection plate 231. The connection ring 232 may be provided in a shape of an annular strip having one side opened in the circumferential direction by the slit 230a.

Although not shown, the connection plate 231 may be provided with a plurality of electrical line connection parts corresponding to the number of the electrical lines. The electrical line connection part may be formed in the circumferential direction of the connection plate 231.

Based on one connection plate 231, one specific electrical line may be connected to any one of the electrical line connection parts and connected to the connection ring 232 provided in the corresponding connection plate 231.

Accordingly, when the connection plates 231 arranged in one direction are viewed from the front, the electrical lines may be connected to the corresponding connection rings 232, respectively, while being spaced apart from each other in the circumferential direction without overlapping with each other.

Meanwhile, the rotational module 230 according to one embodiment of the present invention may further include a multi-contact plate 233.

The multi-contact plate 233 may have at least two contact points at different positions in the circumferential direction on a surface of the connection ring 232 to electrically connect the connection ring 232 and the translational motor driver (not shown).

Accordingly, even though any one contact point is disconnected by the slit 230a when the connection plate 231 is rotated, the other contact point is continuously maintained, and thus the electrical connection state between the connection ring 232 and the translational motor driver may be continuously maintained.

According to one embodiment of the present invention, a plurality of multi-contact plates 233 may be provided. The multi-contact plates 233 may be connected to the connection rings 232, respectively. Accordingly, the multi-contact plates 233 may also be arranged in the same direction as the arrangement direction of the connection rings 232.

In this case, according to one embodiment of the present invention, the multi-contact plates 233 may be offset to each other in one direction to prevent interference between the multi-contact plates 233 arranged in the one direction.

For example, based on the rotational gears 236, the multi-contact plates 233 disposed in an odd-numbered order may be disposed at a lower left end of the connection ring 232, and the multi-contact plates 233 disposed in an even-numbered order may be disposed at a lower right end of the connection ring 232.

The multi-contact plate 233 according to one embodiment of the disclosure may have two contact points with respect to the connection ring 232.

Although not specifically shown, the multi-contact plate 233 may be formed of a metal material having conductivity and include a main body portion and branch portion.

The main body portion may be provided as a plate shape extending in one direction. The branch portion may be branched into two branches from one end of the main body portion in the longitudinal direction.

As described above, one ends of the branch portion extending in the longitudinal direction and branched into the two branches may come into contact with the surface of the connection ring 232. In other words, the two branches of the branch portion may come into contact with the surface of the connection ring 232 at different positions in the circumferential direction.

The branch portion is branched into the two branches merely as one example, and the branch portion may be branch into more branches to come into contact with several positions on the surface of the connection ring 232.

Although not specifically shown, the rotational module 230 may further include a base unit and a power supply unit.

The base unit supports the multi-contact plate 233. Specifically, the main body portion of the multi-contact plate 233 may be coupled and fixed to the base unit. Accordingly, the branch portion of the multi-contact plate 233 may maintain a stable contact with the connection ring 232.

The power supply 235 may be mounted on the base unit. The power supply unit may be electrically connected to the multi-contact plate 233. Accordingly, the power supply unit may supply power to the translational motor 221 and the translational motor driver through the multi-contact plate 233, the connection ring 232, and the electrical line.

In the initial setting for inserting the conduit 20 and the guide wire 10 into the target blood vessel, the front end of the guide wire may be disposed at a branch point side of the branch portion 125 forming the first Y-shaped connector 120, by the roller module 220.

In addition, the guide wire 10 may be drawn into the conduit 20 by the roller module 220 and may be inserted near the target vessel through subsequent translational motions. The guide wire 10 may be rotated by the rotational module 230 when encountering a curved site of the blood vessel during the translational motion, and thus the direction of the front end thereof is switched, thereby allowing the translational motion to be smoothly performed again.

In addition, when the insertion of the conduit 20 into the target blood vessel is completed, the guide wire 10 is moved rearward by the roller module 220, so that the front end thereof returns to the initial setting position.

Referring back to FIGS. 6 and 7, the micro-conduit driving unit 300 may be provided at rear of the conduit driving unit 100.

When the guide wire 10 is drawn out from the inside of the conduit and returned to the initial setting position, the micro-conduit driving unit 300 draws the micro-conduit 40 into a path different from the path for drawing in and out the guide wire 10, that is, into a path coaxial to the conduit 20, thereby translating the micro-conduit 40.

The micro-conduit driving unit 300 according to one embodiment of the present invention may include a front end mounting portion 300A and a rear end mounting portion 300B.

The front end mounting portion 300A may be directly connected to the conduit driving unit 100. The front end mounting portion 300A may be mounted therein with the longitudinal front end part of the micro-conduit 40. The front end mounting portion 300A may have a driving means for rotating and translating the micro-conduit 40.

Since detailed configurations and operations of the driving means are the same as or similar to the detailed configurations and operations of the roller module 220 and the rotational module 230 applied to the guide wire driving unit 200, a detailed description thereof will be omitted.

In the initial setting for inserting the conduit 20 and the guide wire 10 into the target vessel, since the front end mounting portion 300A is directly connected to the conduit driving unit 100, the front end mounting portion 300A is moved together when the conduit driving unit 100 is moved.

In the initial setting for inserting the conduit 20 and the guide wire 10 into the target blood vessel, the longitudinal front end of the micro-conduit 40 is not mounted on the front end mounting portion 300A.

When the insertion of the conduit 20 into the target blood vessel is completed and the front end of the guide wire 10 is returned to the initial setting position, the longitudinal front end of the micro-conduit 40 may be mounted on the front end mounting portion 300A.

The rear end mounting portion 300B is spaced apart rearward from the front end mounting portion 300A. When the front end mounting portion 300A is moved by the movement of the conduit driving unit 100 during the initial setting for inserting the conduit 20 and the guide wire 10 into the target blood vessel, the rear end mounting portion 300B may maintain a home position state without being interlocked with the above movement. The rear end mounting portion 300B may be connected to the micro-guide wire driving unit 400.

The rear end of the micro-conduit 40 is mounted to the rear end mounting portion 300B. The rear end mounting portion 300B may include a third Y-shaped connector 330 (in FIG. 16) for rear end mounting of the micro-conduit 40. The third Y-shaped connector 330 (FIG. 15) may have the same structure as the first and second Y-shaped connectors 120 and 210.

The third Y-shaped connector 330 serves to provide a connection path through which the micro-guide wire 30 positioned at the other end in the longitudinal direction may be inserted into the micro-conduit mounted at one end in the longitudinal direction.

After the insertion of the micro-conduit 40 into the target blood vessel is completed and the front end of the guide wire 10 is returned to the initial setting position, the micro-conduit 40 may be first set to have a first tension when the micro-conduit 40 is set to be mounted to the micro-conduit driving unit 300 in order to insert the micro-conduit 40 and the micro-guide wire 30 into the target micro-vessel.

In other words, as shown in drawings, the micro-conduit 40 may be loosely connected between the front end mounting portion 300A and the rear end mounting portion 300B.

In this state, in order to perform the vascular intervention procedure, the driving means provided at the front end mounting portion 300A forwardly translates the front end of the micro-conduit 40 having the longitudinal rear end fixed to the rear end mounting portion 300B and accordingly, inserts the micro-conduit 40 into the conduit 20.

Accordingly, during the vascular intervention, the micro-channel has a second tension increased in intensity compared with having the first tension (see FIG. 19). In other words, the micro-conduit 40 may be changed from the loose state to a taut state.

The rear end mounting portion 300B may include a micro-conduit translational driving body 340 (see FIG. 15).

The micro-conduit translational driving body 340 provides power for moving the rear end mounting portion 300B, and accordingly, the micro-conduit 40 is translated. The micro-conduit translational driving body 340 may be synchronized with the conduit translational driving body 150 that provides power for moving the conduit driving unit 100.

Accordingly, when the rear end mounting portion 300B is moved by the micro-conduit translational driving body 340 to translate the micro-conduit 40 during the vascular intervention procedure, the conduit driving unit 100 and the front end mounting portion 300A connected thereto are moved at the same speed and distance as those of the rear end mounting portion 300B by the conduit translational driving body 150 synchronized therewith, so that the second tension of the micro-conduit may be continuously maintained during the vascular intervention procedure.

When the conduit 20 and the micro-conduit 40 reach an end of the blood vessel that meets the micro-blood vessel through the synchronization of the micro-conduit translational driving body 340 and the conduit translational driving body 150, the synchronization between the micro-conduit translational driving body 340 and the conduit translational driving body 150 may be released and only the micro-conduit translational driving body 340 may be driven. Accordingly, only the micro-conduit 40 continues to perform translational motion inside the micro-blood vessel.

The micro-guide wire driving unit 400 may be provided at rear of the micro-conduit driving unit 300, more specifically, the rear end mounting portion 300B. The micro-guide wire driving unit 400 may translate the micro-guide wire 30 to draw the micro-guide wire 30 into the micro-conduit 40 and insert the micro-guide wire 30 to the vicinity of the target micro-vessel, and may rotate the micro-guide wire 30 coaxially with the micro-conduit 40.

The front end of the micro-guide wire 30 mounted on the micro-guide wire driving unit 400 may be disposed at the other end in the longitudinal direction of the third Y-shaped connector 330 provided in the rear end mounting unit 300B.

Similar to the guide wire driving unit 200, the line-contact roller mechanism may be applied to the micro-guide wire driving unit 400. The line-contact roller mechanism may be implemented by the roller module 420 having the same function and action as the roller module 220 provided in the guide wire driving unit 200. In addition, since the micro-guide wire driver 400 may include a rotational module 430 having the same function and action as the rotational module 230 provided in the guide wire driving unit 200, a detailed description thereof will be omitted.

Upon the setting to insert the micro-conduit 40 and the micro-guide wire 30 into the target micro-vessel, the micro-guide wire 30 is mounted to the micro-guide wire driving unit 400. The micro-guide wire may be translated by the roller module 420, drawn into the micro-conduit 40, and inserted near the target micro-vessel.

In addition, when the translating micro-guide wire 30 encounters a curved site of the micro-vessel, the micro-guide wire 30 may be rotated by the rotational module 430, and accordingly, a direction of the front end of the micro-guide wire 30 may be adjusted. As a result, the micro-guide wire 30 may be continuously translated toward the target micro-blood vessel.

Meanwhile, the transfer unit 500 may receive driving force from the conduit translational driving body 150 and the micro-conduit translational driving body 340 to transfer the conduit driving unit 100 and the micro-conduit driving unit 300 in the longitudinal direction of the conduit 20.

The transfer unit 500 may include a base portion 510, a first partition wall 520, a second partition wall 530, a support rod 540, a rack 550, and a pinion 560.

The base portion 510 may be a frame that provides a base surface of the vascular intervention robot 1000. The first partition wall 520 and the second partition wall 530 may be provided at both ends of the base portion 510 in the longitudinal direction. The support rod 540 may be provided between the first partition 520 and the second partition 530. The rack 550 may be provided on an upper surface of the base portion 510 in the longitudinal direction of the vascular intervention robot 1000. The pinion 560 may be gear-coupled to the rack 550 and operated by receiving the driving force from the conduit translational driving body 150 or the micro-conduit translational driving body 340. Accordingly, the conduit driving unit 100 and the micro-conduit driving unit 300 mounted in the assembly of the rack 550 and the pinion 560 may be moved in the longitudinal direction of the vascular intervention robot 1000.

The pinion 560 may be connected to each of the conduit driving unit 100 and the micro-conduit driving unit 300 so as to allow the conduit driving unit 100 and the micro-conduit driving unit 300 to be individually moved, and the conduit translational driving body 150 and the micro-conduit translational driving body 340 may provide a driving force to the pinion 560 connected to the conduit driving unit 100 and the micro-conduit driving unit 300, respectively.

Meanwhile, the support rod 540 may provide a guide path for moving the conduit driving unit 100 and the micro-conduit driving unit 300.

The conduit guide unit 600 may perform a function of supporting the conduit 20 while being folded in the longitudinal direction of the conduit 20. The conduit guide unit 600 may be provided in the form of a tube extending in one direction. The conduit guide unit 600 may have a hollow formed therein in the longitudinal direction to allow the conduit 20 to be inserted and moved, and longitudinal both ends thereof may be opened.

In one embodiment of the present invention, the conduit guide unit 600 may have a telescope structure so as to be folded.

Hereinafter, a method of driving the vascular intervention robot according to one embodiment of the present invention will be described with reference to FIGS. 15 to 22.

FIG. 15 is a flowchart sequentially showing a method of driving the vascular intervention robot according to one embodiment of the present invention, and FIGS. 16 to 22 are reference views for describing each step of the method of driving the vascular intervention robot according to one embodiment of the present invention.

Referring to FIG. 15, the vascular intervention robot according to one embodiment of the present invention may be driven through steps S110 to S160.
Step S110

Referring to FIG. 16, step S110 is an initial setting step in which the conduit 20 is mounted in the conduit guide unit 600. In this step, the rear end of the conduit 20 in the longitudinal direction is drawn in and gripped by the longitudinal one end of the main body 123 forming the first Y-shaped connector 120.

In addition, in step S110, the guide wire 10 is longitudinally loaded into the slits 230a of the connection plates 231 and the slits of the rotational gears 236 foaming the single trench structure.

Next, in step S110, the rotational module 220 is driven to dispose the front end of the guide wire 10 to reach the branch point of the branch portion 125 forming the first Y-shaped connector 120. In other words, in step S110, the guide roller 223 may be lowered to come into contact with the guide wire 10 entering the drive roller 222, and then the translational motor 221 may be operated so that the front end of the guide wire 10 may reach the branch point side of the branch portion 125 forming the first Y-shaped connector 120.

In the initial setting step, the micro-conduit 40 and the micro-guide wire 30 are not mounted in the micro-conduit driving unit 300 and the micro-guide wire driving unit 400.
Step S120

Referring to FIG. 17, in step S120, the roller module 220 is driven so that the guide wire 10 disposed at the branch portion 125 side is translated, thereby drawing the guide wire 10 into the conduit 20.

In other words, in step S120, the guide roller 223 may be lowered to come into contact with the guide wire 10 entering the drive roller 222, and then the translational motor 221 may be operated to draw the guide wire 10 into the conduit 20. At this time, the guide roller 223 may be already lowered through step S110.

Next, in step S120, the roller module 220 is driven to continuously translate the guide wire 10, thereby inserting the guide wire 10 into the vicinity of the target blood vessel.

At this time, in step S120, the rotational module 230 may be driven to rotate the translating guide wire 10 when the translating guide wire 10 encounters a bent site of the blood vessel, thereby adjusting the front end direction of the guide wire 10. Accordingly, the guide wire 10 may be smoothly inserted to the vicinity of the target blood vessel.

The guide wire 10 may be rotated by the rotation of the roller module 220 rotated by the rotational module 230. The translational motor 221 is also rotated together when the roller module 220 is rotated.

The electrical line electrically connected between the translational motor driver and the translational motor 221 may be maintained in a stable connection state by the connection ring 232 of the rotational module 230.

In addition, even when the connection ring 232 having one side opened in the circumferential direction is rotated, the electrical connection state may be maintained constantly by the multi-contact plate 233.

Meanwhile, in step S120, the guide wire 10 is inserted into the vicinity of the target blood vessel, and then the conduit translational driving body 150 is driven to translate the conduit 20, thereby inserting the conduit 20 up to the target blood vessel.

The translational motion of the conduit 20 may be performed by the movement of the conduit driving unit 100. In addition, when the conduit driving unit 100 is moved, the front end mounting unit 300A of the micro-conduit driving unit 300 directly connected to the rear of the conduit driving unit is also moved together.

In step S120, like the guide wire 10, when the moving vessel 20 encounters the curved site of the blood vessel, the conduit rotation driving body 110 may be driven to rotate the translating conduit 20, thereby adjusting the front end direction of the conduit 20.

Accordingly, the conduit 20 may be smoothly inserted up to the target blood vessel.
Step S130

Referring to FIG. 18, in step S130, while the conduit 20 is inserted to the target blood vessel, the roller module 220 of the guide wire driving unit 200 is driven to move the guide wire 10 rearward, thereby returning the guide wire 10 to the initial setting position. Accordingly, the front end of the guide wire 10 in the longitudinal direction is positioned at a branch point side of the branch portion 125.

US 12,558,173 B2

19

20

Step S140

Referring to FIG. 19, in step S140, the micro-conduit 40 is mounted in the micro-conduit driving unit 300. Specifically, in step S140, the longitudinal front end of the micro-conduit 40 is mounted to the front end mounting portion 300A, and the longitudinal rear end thereof is mounted to the rear end mounting portion 300B spaced apart rearward from the front end mounting portion 300A.

In the step S140, the micro-conduit 40 may be mounted such that the longitudinal front end of the micro-conduit 40 is positioned at the longitudinal other end of the main body 123 forming the first Y-shaped connector 120.

In step S140, the micro-conduit 40 may be mounted such that the micro-conduit 40 has the first tension. In other words, in step S140, the micro-conduit 40 may be loosely mounted as shown in the drawing.

Meanwhile, in step S140, after the micro-conduit 40 is mounted, the micro-guide wire 30 may be mounted to the micro-guide wire driving unit 400.

In step S140, the micro-guide wires 30 may be longitudinally loaded in the slits of the connection plates and the slits of the rotational gears forming the single trench structure.

Step S150

Referring to FIG. 20, in step S150, the driving means provided in the front end mounting portion 300A is driven to forwardly translate the front end of the micro-conduit 40 having the longitudinal rear end fixed to the rear end mounting portion 300B, thereby drawing the micro-conduit 40 into the conduit 20.

Accordingly, the micro-conduit 40 has the second tension increased in intensity compared with having the first tension set during setting. In other words, the micro-conduit 40 may be changed from a loose state upon setting to a taut state as shown in the drawing.

Step S160

Referring to FIGS. 21 and 22, in step S160, the roller module 420 provided in the micro-guide wire driving unit 400 is driven to translate the micro-guide wire 30, thereby drawing the micro-guide wire 30 into the micro-conduit 40.

Next, in step S160, the roller module 420 is driven to translate the micro-guide wire 30, thereby inserting the micro-guide wire 30 into the vicinity of the target micro-vessel.

In S160, when the translatable micro-guide wire 30 encounters a curved site of the micro-vessel, the rotational module 430 provided in the micro-guide wire driving unit 400 may be driven to rotate the translatable micro-guide wire 30, thereby adjusting the front end direction of the micro-guide wire 30.

Accordingly, the micro-guide wire 30 may be smoothly inserted to the vicinity of the target micro-vessel.

The micro-guide wire 30 may be rotated by the rotation of the roller module 420 rotated by the rotational module 430, and the translational motor is also rotated together when the roller module 420 is rotated. The electrical line electrically connected between the translational motor driver and the translational motor may be maintained in a stable connection state by the connection ring.

In addition, even when the connection ring having one side opened in the circumferential direction is rotated, the electrical connection state may be constantly maintained by the multi-contact plate.

Next, in step S160, the micro-guide wire 30 is inserted into the vicinity of the target micro-vessel, and then the micro-conduit translational driving body 340 is driven to translate the micro-conduit 40, thereby inserting the micro-conduit 40 up to the target micro-vessel. The translational motion of the micro-conduit 40 may be performed by the movement of the micro-conduit driving unit 300.

Since the micro-conduit translational driving body 340 may be synchronized with the conduit translational driving body 150 provided in the conduit driving unit 100, the conduit driving unit 100 and the front end mounting portion 300A connected thereto are also moved together when the micro-conduit driving unit 300 is moved by the micro-conduit translational driving body 340. Accordingly, the micro-conduit may be maintained in the second tension, that is, in the taut state.

In step S160, the micro-conduit translational driving body 340 and the conduit translational driving body 150 are synchronized to each other up to the end part of the blood vessel meeting the micro-blood vessel, so that the conduit 20 and the micro-conduit 40 may be translated together.

However, the conduit 20 having a relatively large diameter cannot be inserted into the micro-blood vessel any more. Thus, in step S160, when the micro-conduit 20 and the micro-conduit 40 reach the end of the blood vessel to meet the micro-blood vessel, the synchronization between the micro-conduit translational driving body 340 and the conduit translational driving body 150 may be released, and then only the micro-conduit translational driving body 340 may be driven.

Accordingly, the micro-conduit 20 may stop the translational motion at the end of the blood vessel that meets the micro-blood vessel, and the micro-conduit 40 may be continuously translated into the micro-blood vessel, so as to be inserted until the target micro-blood vessel.

Although not shown, the driving and releasing the synchronization between the micro-conduit translational driving body 340 and the conduit translational driving body 150 may be controlled by a control unit. The control unit may be provided on a master device side of the vascular intervention system.

Although the present invention has been described in detail using preferred embodiments, the scope of the present invention is not limited to a specific embodiment and will be interpreted by the appended claims. In addition, it will be understood by those skilled in the art that various modifications and deformations are possible without departing from the scope of the present invention.

The invention claimed is:

1. A vascular intervention robot having a line-contact roller mechanism, the vascular intervention robot comprising:

a roller module for translating a medical wire; and a rotational module for rotating the roller module to axially rotate the medical wire, wherein the roller module includes:

a translational motor for providing a translational driving force for translating the medical wire;

at least one drive roller receiving the translational driving force from the translational motor, arranged in a longitudinal direction of the medical wire, and coming into rolling contact with a lower side of the medical wire; and a plurality of guide rollers provided in a number corresponding to a number of the at least one drive roller and arranged on the at least one drive roller in the longitudinal direction of the medical wire, so as to be shifted to one side in the longitudinal direction of the medical wire with respect to the at least one drive roller and coming into rolling contact with an upper side of the medical wire.

2. The vascular intervention robot of claim 1, wherein the at least one drive roller and the guide roller have an overlapping region partially overlapping in a vertical direction, and the medical wire positioned between the at least one drive roller and the guide roller comes into line contact with the at least one drive roller and the guide roller in the overlapping region.

3. The vascular intervention robot of claim 2, wherein the medical wire is moved in a curved line to have a sine wave form and passes through the roller module.

4. The vascular intervention robot of claim 1, wherein the at least one drive roller includes a first drive roller and a second drive roller, and the roller module further includes a belt pulley, in which the belt pulley connects the first drive roller to the translational motor, and the second drive roller is interlocked with rotation of the first drive roller.

5. The vascular intervention robot of claim 4, wherein the roller module includes:

a driving gear coupled to a rotational shaft of the first drive roller;

a driven gear coupled to a rotational shaft of the second drive roller; and an idle gear gear-coupled between the driving gear and the driven gear to rotate the driven gear in a same direction as a rotation direction of the driving gear.

6. The vascular intervention robot of claim 1, wherein the roller module further includes a housing for accommodating the at least one drive roller and the guide roller, and an elevating unit installed in the housing to elevate the guide roller in a vertical direction with respect to the at least one drive roller, and the elevation unit vertically lowers the guide roller to guide a translational motion of the medical wire while the guide roller is rotated relative to the at least one drive roller when the medical wire enters the at least one drive roller.

7. The vascular intervention robot of claim 6, wherein the elevating unit includes:

a base for supporting the guide roller above the guide roller;

a roller fixing block spaced apart above the base;

a roller shaft passing through the base and connecting the guide roller to the roller fixing block; and a spring member provided on an outer circumferential surface of the roller shaft in the longitudinal direction, and interlocked with a descending motion of the roller fixing block coming into close contact with the base to elastically press the guide roller downward so that the guide roller presses the medical wire.

8. The vascular intervention robot of claim 7, wherein the roller module includes:

a hinge cover for opening and closing the housing and pressing the roller fixing block downward by a coupling force applied to the housing when the housing is closed;

a knob fixing block provided on the hinge cover; and a bolt-type knob coupled to the knob fixing block to provide a pressing force to the spring member through the base while descending from the knob fixing block when being rotated.

9. The vascular intervention robot of claim 1, wherein the medical wire includes any one of a guide wire configured to be inserted into a conduit configured to be inserted into a human body and a micro-guide wire configured to be inserted into a micro-conduit configured for insertion into the conduit.

10. The vascular intervention robot of claim 9, further comprising:

a conduit driving unit, wherein the conduit driving unit rotates and translates the conduit extending in the longitudinal direction around the longitudinal direction as an axis.

11. The vascular intervention robot of claim 10, wherein the guide wire is translated into the conduit by the roller module, and rotated coaxially to the conduit by rotation of the roller module by the rotational module.

12. The vascular intervention robot of claim 10, further comprising:

a micro-conduit driving unit, wherein the micro-conduit driving unit is provided at a rear side of the conduit driving unit to translate the micro-conduit along a path coaxial to the conduit and different from a path through which the guide wire is drawn in and out with respect to the conduit when the guide wire is drawn out from the inside of the conduit.

13. The vascular intervention robot of claim 12, wherein the micro-guide wire is translated toward the inside of the micro-conduit by the roller module, and rotated coaxially to the micro-conduit by rotation of the roller module by the rotational module.

14. A vascular intervention system comprising:

a vascular intervention robot of claim 1; and a frame fixing the vascular intervention robot so as to be movable relative to a surgical bed.

* * * * *